US009822367B2

(12) United States Patent
Sapieha

(10) Patent No.: US 9,822,367 B2
(45) Date of Patent: Nov. 21, 2017

(54) INHIBITION OF SEMA3A IN THE PREVENTION AND TREATMENT OF OCULAR HYPERPERMEABILITY

(71) Applicant: RSEM, LIMITED PARTNERSHIP, Montreal (CA)

(72) Inventor: Przemyslaw Sapieha, Montreal (CA)

(73) Assignee: RSEM, LIMITED PARTNERSHIP, Montreal (CA)

(*) Notice: Subject to any disclaimer, the term of this patent is extended or adjusted under 35 U.S.C. 154(b) by 0 days.

(21) Appl. No.: 14/769,255

(22) PCT Filed: Feb. 21, 2014

(86) PCT No.: PCT/CA2014/050119
§ 371 (c)(1),
(2) Date: Aug. 20, 2015

(87) PCT Pub. No.: WO2014/127479
PCT Pub. Date: Aug. 28, 2014

(65) Prior Publication Data
US 2016/0002641 A1 Jan. 7, 2016

Related U.S. Application Data

(60) Provisional application No. 61/767,419, filed on Feb. 21, 2013.

(51) Int. Cl.
*A61P 27/02* (2006.01)
*A61P 9/10* (2006.01)
(Continued)

(52) U.S. Cl.
CPC ........ *C12N 15/1138* (2013.01); *A61K 9/0048* (2013.01); *A61K 31/7088* (2013.01); *A61K 31/713* (2013.01); *A61K 38/17* (2013.01); *A61K 38/179* (2013.01); *C07K 16/18* (2013.01); *C12Q 1/6897* (2013.01); *G01N 33/5023* (2013.01); *G01N 33/6893* (2013.01); *A61K 35/30* (2013.01); *A61K 2039/505* (2013.01);
(Continued)

(58) Field of Classification Search
None
See application file for complete search history.

(56) References Cited

U.S. PATENT DOCUMENTS

2015/0368327 A1   12/2015 Goshima et al.

FOREIGN PATENT DOCUMENTS

| WO | 99/29858 A1 | 6/1999 |
| WO | 2010/027743 A1 | 3/2010 |
| WO | PCT/CA2014/050119 | 5/2014 |

OTHER PUBLICATIONS

Cerani et al., Semaphorin 3A Promotes Vascular Leakage in Diabetic Retinopathy. ARVO Annual Meeting Abstract, vol. 53 (14) Mar. 2012. Downloaded May 20, 2016.*

(Continued)

*Primary Examiner* — Adam M Weidner
*Assistant Examiner* — Aurora M Fontainhas
(74) *Attorney, Agent, or Firm* — Julie Gauvreau

(57) ABSTRACT

Described herein is a method of preventing or treating ocular vascular hyperpermeability including macular edema, in a subject comprising inhibiting Sema3A activity. Also disclosed are compositions and their use for preventing or treating Sema3A-dependent ocular vascular hyperpermeability.

13 Claims, 11 Drawing Sheets

(51) Int. Cl.
| | |
|---|---|
| C12N 15/113 | (2010.01) |
| C12P 21/08 | (2006.01) |
| G01N 33/15 | (2006.01) |
| A61K 38/17 | (2006.01) |
| G01N 33/50 | (2006.01) |
| A61K 31/7088 | (2006.01) |
| A61K 31/713 | (2006.01) |
| C07K 16/18 | (2006.01) |
| A61K 9/00 | (2006.01) |
| C12Q 1/68 | (2006.01) |
| G01N 33/68 | (2006.01) |
| A61K 39/00 | (2006.01) |
| A61K 35/30 | (2015.01) |

(52) U.S. Cl.
CPC ...... C07K 2317/76 (2013.01); C12N 2310/14 (2013.01); C12N 2310/531 (2013.01); C12N 2320/30 (2013.01); G01N 2333/705 (2013.01); G01N 2500/10 (2013.01); G01N 2800/164 (2013.01)

(56) References Cited

OTHER PUBLICATIONS

Arvo e-mail communication on Nov. 7, 2016.*
Dhimolea, Canakinumab, MAbs. Jan.-Feb. 2010;2(1):3-13. Epub Jan. 15, 2010.*
Gu et al., Characterization of Neuropilin-1 Structural Features That Confer Binding to Semaphorin 3A and Vascular Endothelial Growth Factor 165*. The Journal of Biological Chemistry vol. 277, No. 20, Issue of May 17, pp. 18069-18076, 2002.*
Joyal et al., Ischemic neurons prevent vascular regeneration of neural tissue by secreting semaphorin 3A. Blood, Jun. 2, 2011, vol. 117, No. 22, 6024-6035.*
Cunha-Vaz et al., Nonproliferative retinopathy in diabetes type 2.Initial stages and characterization of phenotypes. Progress in Retinal and Eye Research 24 (2005) 355-377.*
Acevedo et al., Semaphorin 3A suppresses VEGF-mediated angiogenesis yet acts as a vascular permeability factor Blood. (2008);111(5)2674-2680.
Antipenko et al.,Structure of the semaphorin-3A receptor binding module, Neuron (2003), 39: 589-598.
Antonetti et al., Diabetic retinopathy. N Engl J Med. (2012);366(13):1227-1239.
Appleton et al. Structural studies of neuropilin/antibody complexes provide insights into semaphorin and VEGF binding. EMBO J. (2007);26(23):4902-4912.
Calalb et al., Tyrosine phosphorylation of focal adhesion kinase at sites in the catalytic domain regulates kinase activity: a role for Src family kinases. Molecular and cellular biology. (1995);15(2):954-963.
Chen et al., Retinopathy of prematurity. Angiogenesis. (2007);10(2):133-140.
Chen et al. VEGF-induced vascular permeability is mediated by FAK. Developmental cell. (2012);22(1):146-157.
Cheung N., Diabetic retinopathy and systemic vascular complications. Progress in Retinal and Eye Research. (2008);27(2):161-176.
Dull et al., A third-generation lentivirus vector with a conditional packaging system. Journal of virology. (1998);72 (11):8463-8471.
Eliceiri et al., Selective requirement for Src kinases during VEGF-induced angiogenesis and vascular permeability. Molecular cell. (1999);4(6):915-924.
Fukushima et al., Sema3E-PlexinD1 signaling selectively suppresses disoriented angiogenesis in ischemic retinopathy in mice. J Clin Invest. (2011);121(5):1974-1985.
Geretti et al., Neuropilin structure governs VEGF and semaphorin binding and regulates angiogenesis. Angiogenesis. (2008);11(1):31-39.

Gilbert et al., Retinopathy of prematurity in middle-income countries. Lancet. (1997);350(9070):12-14.
Gluzman-Poltorak et al., Vascular endothelial growth factor receptor-1 and neuropilin-2 form complexes. J Biol Chem. (2001);276(22):18688-18694.
Guttman-Raviv et al., Semaphorin-3A and Semaphorin-3F work together to repel endothelial cells and to inhibit their survival by induction of apoptosis. (2007) JBC Papers in Press, Manuscript M609711200.
Hunter T., A tail of two src's: mutatis mutandis. Cell. (1987);49(1):1-4.
Jones et al., Separating genetic and hemodynamic defects in neuropilin 1 knockout embryos. Development. (2008);135(14):2479-2488.
Joyal et al., Ischemic neurons prevent vascular regeneration of neural tissue by secreting semaphorin 3A. Blood. (2011);117(22):6024-6035.
Kawasaki et al., A requirement for neuropilin-1 in embryonic vessel formation. Development. (1999);126 (21):4895-4902.
Kempen et al., The prevalence of diabetic retinopathy among adults in the United States. Arch Ophthalmol. (2004);122(4):552-563.
Kim et al., Semaphorin 3E-Plexin-D1 signaling regulates VEGF function in developmental angiogenesis via a feedback mechanism. Genes Dev. (2011);25(13):1399-1411.
Kitsukawa et al., Neuropilin-semaphorin III/D-mediated chemorepulsive signals play a crucial role in peripheral nerve projection in mice. Neuron. (1997);19(5):995-1005.
Klagsbrun et al., A role for axon guidance receptors and ligands in blood vessel development and tumor angiogenesis. Cytokine Growth Factor Rev. (2005);16(4-5):535-548.
Klagsbrun et al., The role of neuropilin in vascular and tumor biology. Adv Exp Med Biol. (2002);515:33-48.
Lee et al., M. Neuropilin-1 is required for vascular development and is a mediator of VEGF-dependent angiogenesis in zebrafish. Proc Natl Acad Sci U S A. (2002);99(16):10470-10475.
Mamluk et al., Neuropilin-1 binds vascular endothelial growth factor 165, placenta growth factor-2, and heparin via its b1b2 domain. J Biol Chem. (2002);277(27):24818-24825.
Miao et al., Neuropilin-1 mediates collapsin-1/semaphorin III inhibition of endothelial cell motility: functional competition of collapsin-1 and vascular endothelial growth factor-165. J Cell Biol. (1999);146(1):233-242.
Mima et al., Retinal not systemic oxidative and inflammatory stress correlated with VEGF expression in rodent models of insulin resistance and diabetes. Invest Ophthalmol Vis Sci. (2012).
Moss et al., The 14-year incidence of visual loss in a diabetic population. Ophthalmology. (1998);105(6):998-1003.
Potter et al., Tyrosine phosphorylation of VE-cadherin prevents binding of p120- and beta-catenin and maintains the cellular mesenchymal state. J Biol Chem. (2005);280(36):31906-31912.
Robinson et al., Nonvascular role for VEGF: VEGFR-1, 2 activity is critical for neural retinal development. FASEB J. (2001)15(7)1215-1217.
Sapieha et al., Proliferative retinopathies: angiogenesis that blinds. Int J Biochem Cell Biol. (2010);42(1):5-12.
Sapieha et al., The succinate receptor GPR91 in neurons has a major role in retinal angiogenesis. Nature Medicine. (2008)14(10):1067-1076.
Scheppke et al., Retinal vascular permeability suppression by topical application of a novel VEGFR2/Src kinase inhibitor in mice and rabbits. The Journal of clinical investigation. (2008);118(6):2337.
Schlaepfer et al., Integrin-mediated signal transduction linked to Ras pathway by GRB2 binding to focal adhesion kinase, Nature. (1994);372(6508):786-791.
Shirvan et al., Anti-semaphorin 3A Antibodies Rescue Retinal Ganglion Cells from Cell Death following Optic Nerve Axotomy. JBC 277, (2002) (51): 49799-49807.
Silva et al., Effect of systemic medications on onset and progression of diabetic retinopathy. Nat Rev Endocrinol. Sep. 2010;6(9):494-508.

(56) References Cited

OTHER PUBLICATIONS

Smith LE., Through the eyes of a child: understanding retinopathy through ROP the Friedenwald lecture. Invest Ophthalmol Vis Sci. (2008);49(12):5177-5182.
Soker et al., VEGF165 mediates formation of complexes containing VEGFR-2 and neuropilin-1 that enhance VEGF165-receptor binding. J Cell Biochem. (2002);85(2):357-368.
Stahl et al., The mouse retina as an angiogenesis model. Invest Ophthalmol Vis Sci. (2010);51(6):2813-2826.
Stewart MW., The expanding role of vascular endothelial growth factor inhibitors in ophthalmology. Mayo Clin Proc. (2012);87(1):77-88.
Vieira et al., Role of the neuropilin ligands VEGF164 and SEMA3A in neuronal and vascular patterning in the mouse. Novartis Found Symp. (2007);283:230-235; discussion 235-241.
Wang et al., Novel targets against retinal angiogenesis in diabetic retinopathy. Curr Diab Rep. (2012);12(4):355-363.
Geretti E et al., "Neuropilins: novel targets for anti-angiogenesis therapies". Cell Adhesion and Migration, Landes Bioscience, US. vApril 1, 2007. vol. 1 (2), pp. 56-61.
Hruby, Victor J. "Designing Receptor Agonists and antagonists". Nature Reviews Drug Discovery. Nov. 1, 2002. vol. 1 (11), pp. 847-858.
European Search Report and Opinion of corresponding European Application No. EP14754943.

\* cited by examiner a
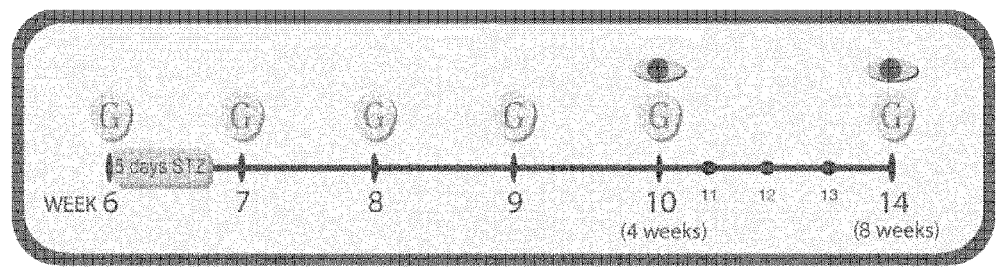
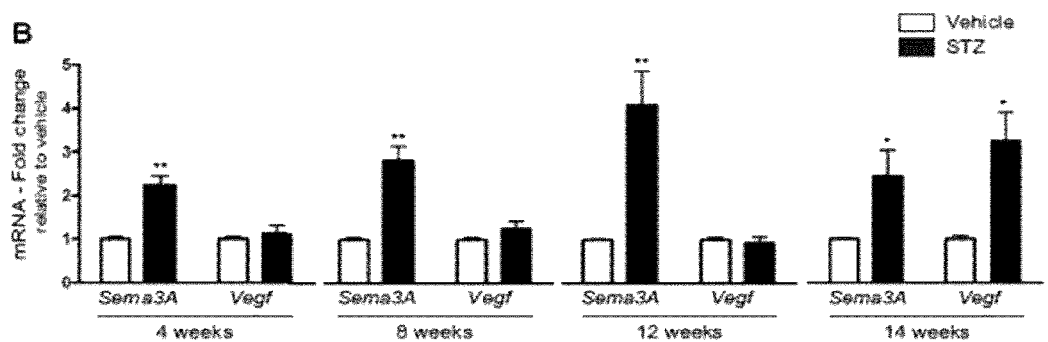
FIGURE 2 (a and b)

c
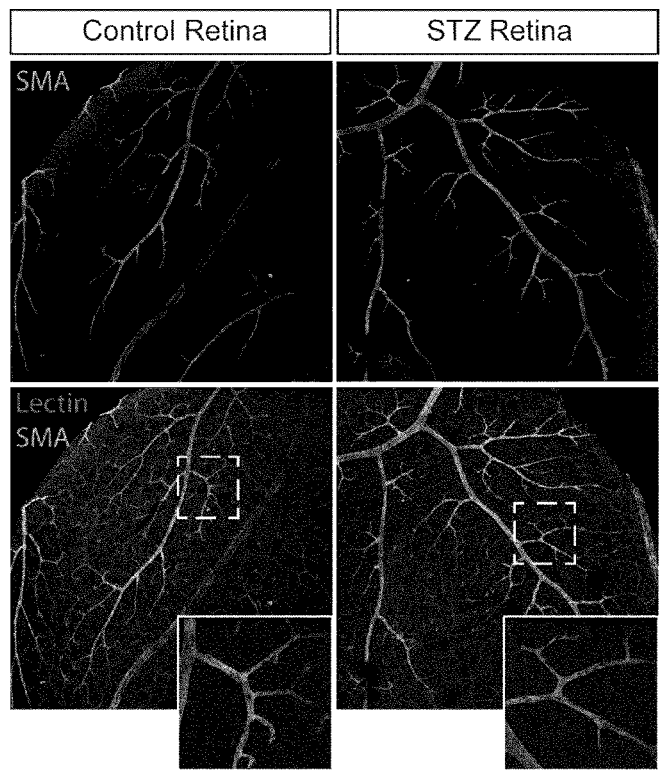
d
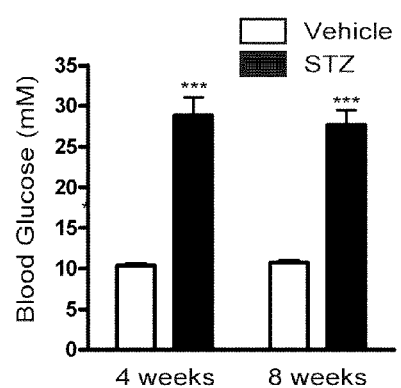
e
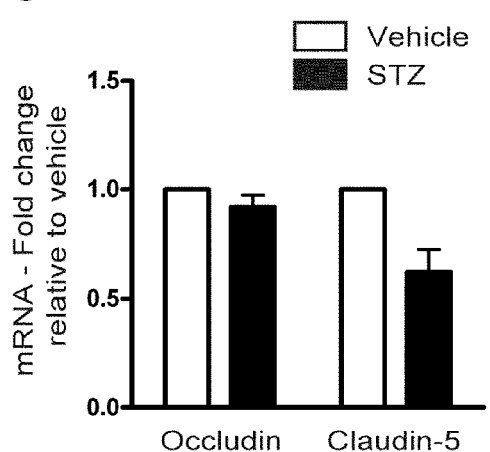
FIGURE 2 (c-e)

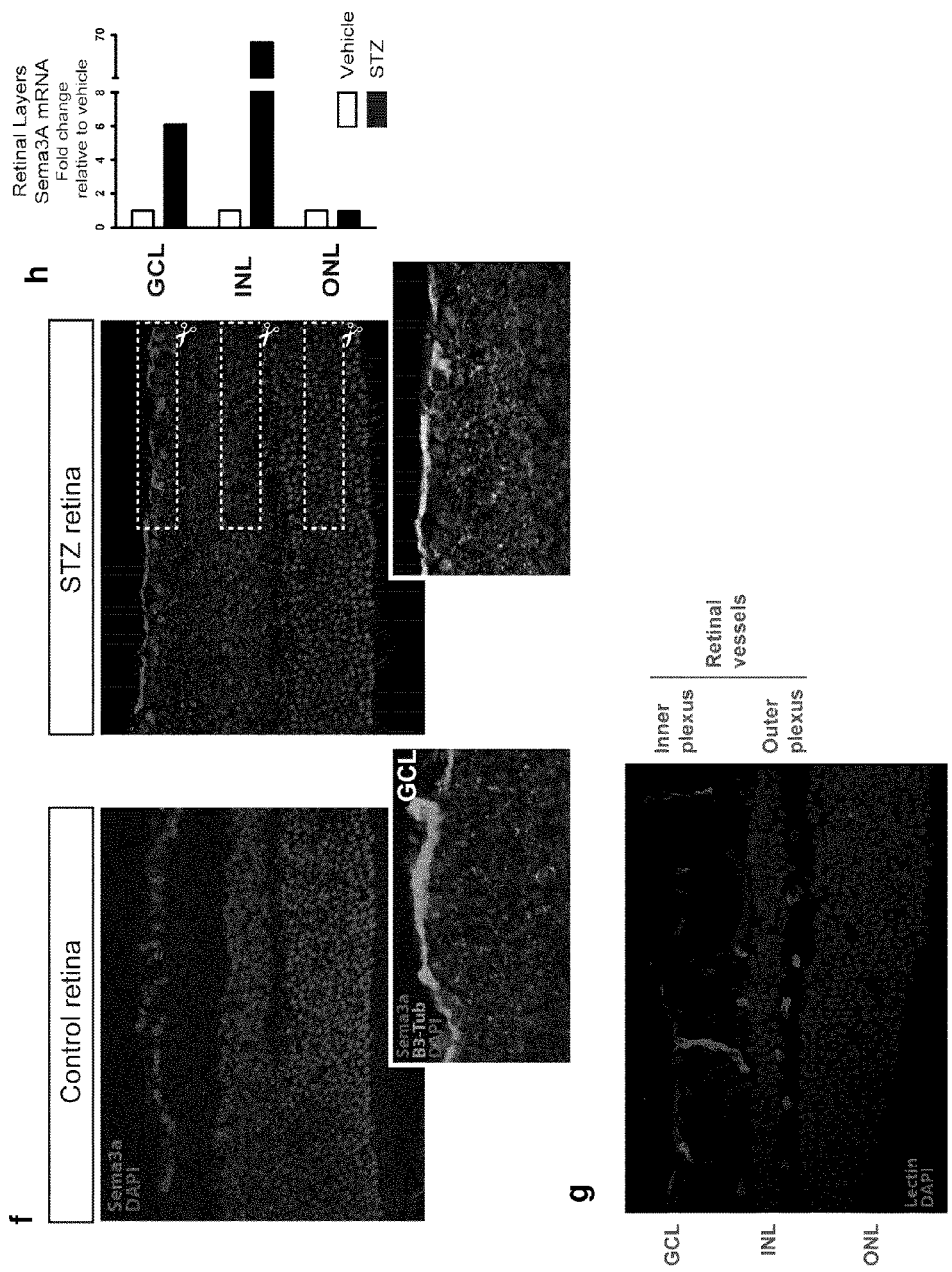
FIGURE 2 (f-h)

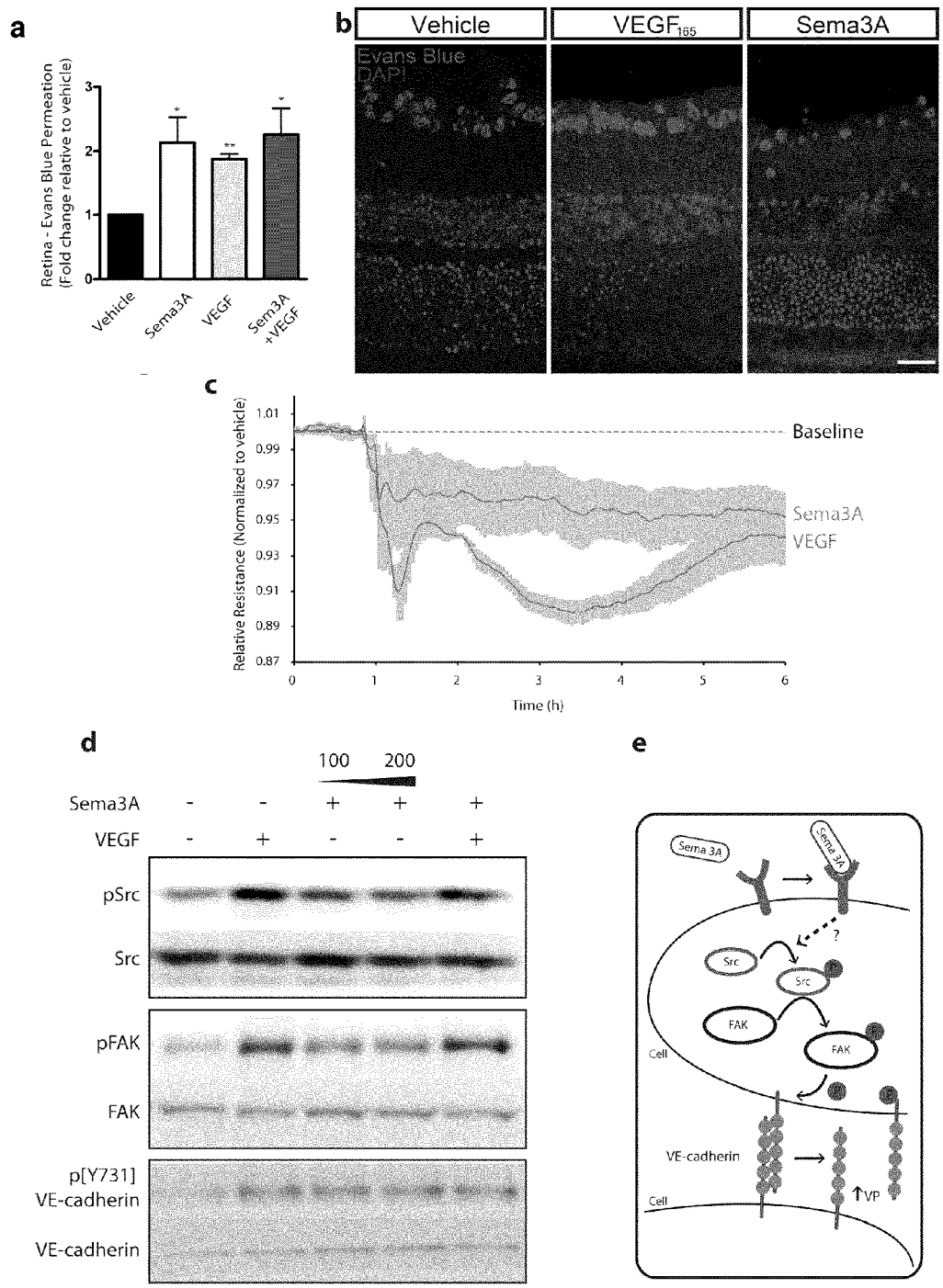
FIGURE 3(a-e)

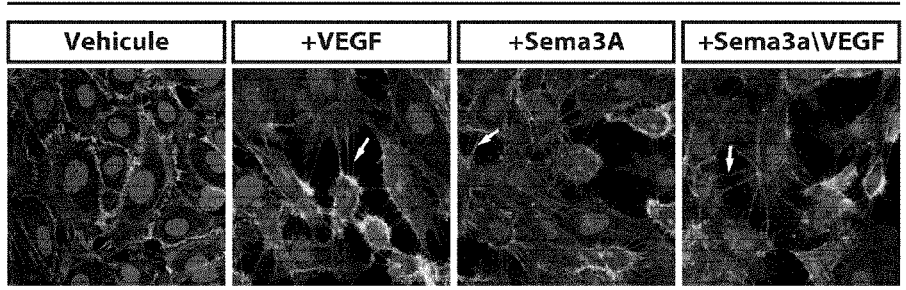
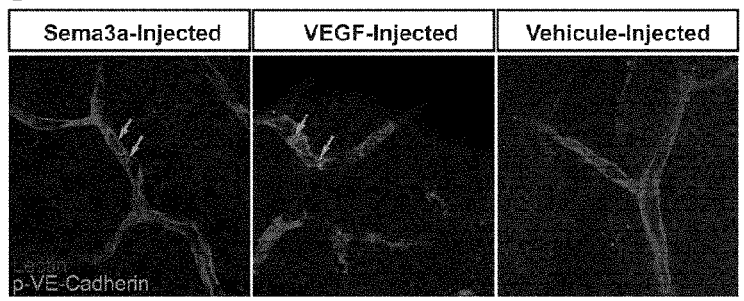
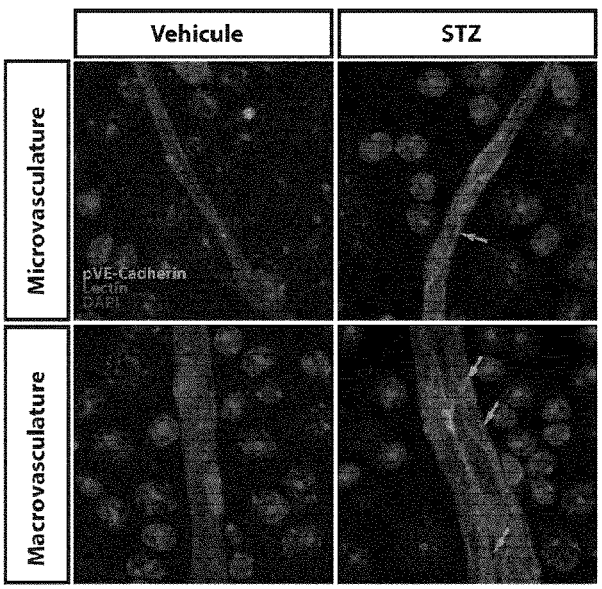
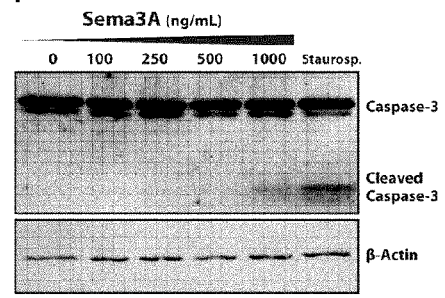
FIGURE 3(f-i)

```
        10         20         30         40         50         60
MGWLTRIVCL FWGVLLTARA NYQNGKNNVP RLKLSYKEML ESNNVITFNG LANSSSYHTF
        70         80         90        100        110        120
LLDEERSRLY VGAKDHIFSF DLVNIKDFQK IVWPVSYTRR DECKWAGKDI LKECANFIKV
       130        140        150        160        170        180
LKAYNQTHLY ACGTGAFHPI CTYIEIGHHP EDNIFKLENS HFENGRGKSP YDPKLLTASL
       190        200        210        220        230        240
LIDGELYSGT AADFMGRDFA IFRTLGHHHP IRTEQHDSRW LNDPKFISAH LISESDNPED
       250        260        270        280        290        300
DKVYFFFREN AIDGEHSGKA THARIGQICK NDFGGHRSLV NKWTTFLKAR LICSVPGPNG
       310        320        330        340        350        360
IDTHFDELQD VFLMNFKDPK NPVVYGVFTT SSNIFKGSAV CMYSMSDVRR VFLGPYAHRD
       370        380        390        400        410        420
GPNYQWVPYQ GRVPYPRPGT CPSKTFGGFD STKDLPDDVI TFARSHPAMY NPVFPMNNRP
       430        440        450        460        470        480
IVIKTDVNYQ FTQIVVDRVD AEDGQYDVMF IGTDVGTVLK VVSIPKETWY DLEEVLLEEM
       490        500        510        520        530        540
TVFREPTAIS AMELSTKQQQ LYIGSTAGVA QLPLHRCDIY GKACAECCLA RDPYCAWDGS
       550        560        570        580        590        600
ACSRYFPTAK RRTRRQDIRN GDPLTHCSDL HHDNHHGHSP EERIIYGVEN SSTFLECSPK
       610        620        630        640        650        660
SQRALVYWQF QRRNEERKEE IRVDDHIIRT DQGLLLRSLQ QKDSGNYLCH AVEHGFIQTL
       670        680        690        700        710        720
LKVTLEVIDT EHLEELLHKD DDGDGSKTKE MSNSMTPSQK VWYRDFMQLI NHPNLNTMDE
       730        740        750        760        770
FCEQVWKRDR KQRRQRPGHT PGNSNKWKHL QENKKGRNRR THEFERAPRS V
```

FIGURE 6

```
  1 merglpllca vlalvlapag afrndkcgdt ikiespgylt spgyphsyhp sekcewliqa
 61 pdpyqrimin fnphfdledr dckydyvevf dgenenghfr gkfcgkiapp pvvssgpflf
121 ikfvsdyeth gagfsiryei fkrgpecsqn yttpsgviks pgfpekypns lectyivfap
181 kmseiilefe sfdlepdsnp pggmfcrydr leiwdgfpdv gphigrycgq ktpgrirsss
241 gilsmvfytd saiakegfsa nysvlqssvs edfkcmealg mesgeihsdq itassqystn
301 wsaersrlny pengwtpged syrewiqvdl gllrfvtavg tqgaisketk kkyyvktyki
361 dvssngedwi tikegnkpvl fqgntnptdv vvavfpkpli trfvrikpat wetgismrfe
421 vygckitdyp csgmlgmvsg lisdsqitss nqgdrnwmpe nirlvtsrsg walppaphsy
481 inewlqidlg eekivrgiii qggkhrenkv fmrkfkigys nngsdwkmim ddskrkaksf
541 egnnnydtpe lrtfpalstr firiyperat hgglglrmel lgceveggtt vlatekptvi
601 dstiqsgik
```

INHIBITION OF SEMA3A IN THE PREVENTION AND TREATMENT OF OCULAR HYPERPERMEABILITY

CROSS REFERENCE TO RELATED APPLICATIONS

This application is a National Entry Application of PCT application no PCT/CA2014/050119 filed on Feb. 21, 2014 and published in English under PCT Article 21(2) which itself claims priority, under 35 U.S.C. §119(e), of U.S. provisional application Ser. No. 61/767,419, filed on Feb. 21, 2013. All documents above are incorporated herein by reference in their entirety.

SEQUENCE LISTING

This application contains a Sequence Listing in computer readable form entitled "12810_553_ST25", created on Aug. 4-18, 2015 having a size of about 40 Kbytes, which is incorporated herein by reference.

FIELD OF THE INVENTION

The present invention relates to ocular vascular hyperpermeability. More specifically, the present invention is concerned with the inhibition of the SEMA3A pathway for the prevention or treatment of macular edema.

BACKGROUND OF THE INVENTION

Diabetic retinopathy (DR) is the most prominent complication of diabetes and the leading cause of blindness in working age individuals[1,2]. It is characterized by an initial microvascular degeneration followed by a compensatory but pathological hyper-vascularization mounted by the hypoxic retina in an attempt to reinstate metabolic equilibrium[3-5]. Although often initially asymptomatic, loss of sight is provoked primarily by diabetic macular edema (DME), vitreal hemorrhages and in advanced cases, pre-retinal neovascularization and tractional retinal detachment[6,7]. Of these, DME is the main cause of central vision loss in diabetics[8], affecting over 25% of patients suffering from diabetes. It is triggered secondary to the deterioration of the blood-retinal barrier (BRB) and the consequent increase in extravasation of fluids and plasma components into the vitreous cavity. Ultimately, the decrease in retinal vascular barrier function leads to vasogenic edema and pathological thickening of the retina.

There are generally 3 stages to diabetic retinopathy: i) non-proliferative retinopathy (NPR); ii) macular edema; and iii) proliferative diabetic retinopathy.

The first stage of diabetic retinopathy, non-proliferative retinopathy or background retinopathy often has no noticeable signs or symptoms, although retinal swelling may be present. This is the stage where the tiny capillaries of the retina become semi-permeable membranes (Later, they will leak fluid and blood.). During the earliest stages, diabetic retinopathy is often asymptomatic. This means that there are no noticeable symptoms—such as pain or vision loss- to the patient, but an eye specialist might find signs of the disease. For example, retinal swelling may be present, which can only be detected through an eye examination.

The second stage of diabetic retinopathy is macular edema. The macula is the part of the retina responsible for sharp, direct vision due to its high density in cones photoreceptors. It is situated at the back of the retina. Macular edema refers to the accumulation of fluid within the retina at the macular area (distinct from the condition where the fluid accumulates under the retina). The pathophysiology depends on the primary cause but usually, the end-point is vascular instability and a breakdown of the blood-retinal barrier, leading to visual impairment.

When the center of the macula begins to swell, vision may become blurry. This middle stage of diabetic retinopathy may overlap the other stages. This is the stage where the blood-retinal barrier is compromised and capillaries in the retina begin to leak fluid, causing swelling and blurred vision.

There are two types of macular edema: focal and diffuse. Focal macular edema occurs when the retinal capillaries develop micro-aneurisms which leak fluid, resulting in several distinct points of leakage. Diffuse macular edema is caused by the dilation of retinal capillaries, creating leakage that is diffused over a general area. The type of macular edema present will determine the kind of diabetic retinopathy treatment. Early detection of macular edema helps ensure the most effective treatment.

As the disease advances, minor visual impairment can occur. Although patients are still able to see, they can be frustrated by blurring and blind spots that inhibit clear vision. These symptoms of diabetic retinopathy are sometimes linked to macular edema, which is the swelling of the part of the eye that controls central vision, known as the macula.

As damaged blood vessels begin to break, blood can leak into the eye. This third stage of diabetic retinopathy, called proliferative diabetic retinopathy (PDR), is characterized by cloudiness and impaired vision. When the retinal capillaries break, they are no longer able to supply the retina with the necessary nutrients. The nutrient-starved retina sends out a chemical signal that prompts the growth of new capillaries. This growth is called neovascularization.

The new blood vessels that form as a result of proliferative diabetic retinopathy cause more damage to the eye. These capillaries are unable to restore nutrients to the retina because they are fragile and weak. They also tend to burst, causing blood and fluid to leak into the eye. The new vessels also exert traction on the surrounding structures and connective tissue, which can eventually detach the retina. Intraocular pressure can also increase as a result of the new capillaries, as they can block the ducts where fluid is drained from the eye. This condition is known as neovascular glaucoma. During proliferative diabetic retinopathy, scar tissue development, retinal detachment, and blindness can occur.

If the disease has progressed into proliferative diabetic retinopathy without the patient receiving any preventative care or medical intervention, retinal detachment and blindness can result. At this time, PDR is the leading cause of new cases of blindness in the United States. Retinal detachment, macular edema, and the breakdown of capillaries in the retina can all prevent normal blood flow through the eye and lead to total vision loss.

Macular edema is not limited to the context of diabetes. Hyperpermeability of blood vessels and leakage of the blood-retinal barrier can occur in a number of circumstances. The most frequent form of macular edema is cystoid macular edema, which is characterized by intraretinal edema contained in honeycomb-like spaces. CME is a common pathological response to a variety of insults (e.g., following intraocular (cataract) surgery, in central and branch retinal vein occlusions, following injury to the eye, in association with choroidal tumors or in various types of vascular retinal diseases or retinal dystrophies). CME is also one of the many conditions that may arise from age-related macular degeneration.

Although significant effort has been invested in elucidating the mechanisms that govern macular edema and in particular destructive pre-retinal neovascularization in DR[6,9,10], considerably less is known about the cellular processes that lead to increased retinal vascular permeability. Consequently, the current standards of care present non-negligible side-effects. These include increased cataract formation and a harmful rise in intraocular pressure with intravitreal use of corticosteroid[9]. Similarly, anti-VEGF (vascular endothelial growth factor) therapies, which in general exhibit respectable safety profiles, may be associated with increased thromboembolic events[11], possible neuronal toxicity and geographic atrophy when used for long term regiments[12,13]. Moreover, the first and most widely used form of treatment is panretinal photocoagulation for either proliferative diabetic retinopathy (PDR) or grid/focal laser for DME. laser-based photocoagulation approaches destroy hypoxic retinal tissue secreting pro-angiogenic factors and inadvertently lead to reduced visual field or central or paracentral scotomas. These therapeutic limitations highlight the need for novel pharmacological targets and interventions.

The present description refers to a number of documents, the content of which is herein incorporated by reference in their entirety.

SUMMARY OF THE INVENTION

Accordingly, Applicant has identified a novel therapeutic target, Sema3A, for the prevention and treatment of retinal vascular hyperpermeability related retinopathy including non-proliferative diabetic retinopathy and macular edema.

Sema3A is a classical neuronal guidance cue also involved in a variety of cellular responses through its binding to Neuropilin-1 (Nrp-1), a non-tyrosine kinase multifunctional receptor. Neuropilin-1 has the particular ability to bind two structurally dissimilar ligands via distinct sites on its extracellular domain[15-17]. It binds Sema3A[18,19] provoking cytoskeletal collapse and $VEGF_{165}$[16,17,19,20] enhancing binding to VEGFR2 and thus increasing its angiogenic potential[21]. Crystallographic evidence revealed that $VEGF_{165}$ and Sema3A do not directly compete for Nrp-1 but rather can simultaneously bind to Nrp-1 at distinct, non-overlapping sites[22]. Moreover, genetic studies show that Nrp-1 distinctly regulates the effects of VEGF and Sema3A on neuronal and vascular development[23]. Notably, it was proposed that, similar to VEGF, Sema3A may itself promote vascular permeability (Acevedo et al., 2008); this is a counterintuitive observation, given the divergent biological roles of VEGF and Sema3A. However, the role of Sema3A in mediating the breakdown of barrier function, such as that observed in diabetic retinopathy, has not been explored to date.

Applicant show herein for the first time that Sema3A is involved in the deterioration of the blood-retinal barrier (BRB) function in diabetic retinopathy. Applicant demonstrates in both human patients and animal models that ocular Sema3A is robustly induced in the early stages of diabetes (prior to VEGF inducement). Applicant further shows that SEMA3A mediates, via NRP1, the breakdown of the inner BRB, leading to increased vascular permeability thereby contributing to retinal swelling and macular edema. Accordingly SEMA3A provides a good target for the prevention of symptoms associated with macular edema or for early treatment of the disease (e.g., in the non-proliferative stage of diabetic retinopathy), prior to substantial pathological neovascularization and damages to the retina. Neutralizing Sema3A thus represents an attractive alternative therapeutic strategy to counter pathologic vascular permeability in DR.

Accordingly, in a first aspect, the present invention provides a method of preventing or treating macular edema in a subject comprising inhibiting Sema3A-mediated cellular activity.

In a related aspect the present invention provides a method of preventing or treating non-proliferative diabetic retinopathy in a subject comprising inhibiting Sema3A-mediated cellular activity.

In another aspect, the present invention provides a method of preventing or treating retinal swelling in a subject comprising inhibiting Sema3A-mediated cellular activity.

In an embodiment, the Sema3A-mediated cellular activity comprises Sema3A-mediated vascular permeability. In a related embodiment, the Sema3A-mediated activity comprises Sema3A binding to the Nrp-1 receptor.

In an embodiment the macular edema is substantially non-proliferative macular edema. In another embodiment, the macular edema is diabetic macular edema. In another embodiment the diabetic macular edema is substantially non-proliferative (i.e., neovascularization is substantially low or absent). In yet a further embodiment, the macular edema is age-related macular edema. In an embodiment, the age related macular edema is substantially non-proliferative.

In an embodiment, the methods of the present invention comprise administering a therapeutically or prophylactically effective amount of a Sema3A antagonist to the subject. In an embodiment, the antagonist reduces Sema3A nucleic acid or protein expression. In another embodiment, the Sema3A antagonist reduces Sema3A secretion. In a further embodiment the Sema3A antagonist reduces Sema3A vitreal concentration. In a further embodiment the Sema3A antagonist reduces Npr-1 ocular (e.g., vitreal) concentration and/or activity. In yet another embodiment, the Sema3A antagonist inhibits Sema3A-mediated cell signaling. In an embodiment, the Sema3A-mediated cell signaling comprises binding of Sema3A to its cognate receptor Npr-1.

In an embodiment, the antagonist is an anti-Sema3A antibody. In an embodiment, the anti-Sema3A antibody specifically inhibits Sema3A binding to Nrp-1 but does not substantially reduce VEGF binding to Nrp-1. In another embodiment, the Sema3A antagonist is an Nrp-1 antibody that inhibits binding of Sema3A to the receptor. In a preferred embodiment, the Nrp-1 antibody does not substantially reduce VEGF binding to Nrp-1. In a particular embodiment, the Nrp-1 antibody binds to the a1, a2 or a1/a2 domain of Nrp-1.

In yet a further embodiment, the Sema3A antagonist is a soluble Nrp-1 polypeptide or fragment thereof that binds to Sema3A. In an embodiment, the fragment comprises domain a1, a2 or a1 and a2 of Nrp-1. In an embodiment, the fragment does not comprise domains b1, b2 or IA and b2 of Npr-1. In a related embodiment, the soluble Nrp-1 fragment does not substantially bind to VEGF. In an embodiment, the fragment comprises domains a1a2 and b1b2 or portions thereof and binds to Sema3A and VEGF.

In another embodiment, the Sema3A antagonist reduces Sema3A or Npr-1 nucleic acid or protein expression. In an embodiment, the Sema3A antagonist is a Sema3A shRNA or antisense. In an embodiment, the Sema3A antagonist is a Npr-1 shRNA or antisense that binds to a polynucleotide encoding a Npr-1 polypeptide, preferably a human Npr-1 polypeptide (e.g., SEQ ID NO:2 or 12).

In a further aspect, the present invention concerns a composition for reducing retinal vascular hyperpermeability comprising one or more of the above-described Sema3A antagonist together with a suitable pharmaceutical carrier.

In yet another aspect, the present invention concerns a composition for the prevention or treatment of vascular hyperpermeability, diabetic retinopathy, macular edema, preferably, age related macular edema, more preferably non-proliferative age-related macular edema and even more preferably, non-proliferative diabetic macular edema comprising one or more of the above-described Sema3A antagonist together with a suitable pharmaceutical carrier.

In a preferred embodiment, the compositions of the present invention are suitable for intraocular administration. In an embodiment, the compositions are formulated in the form of eye drops. In another embodiment, the compositions are formulated for intraocular injection.

In an embodiment, the composition comprises one or more additional active agent useful in the treatment of non-proliferative diabetic retinopathy or macular edema.

In a related aspect, the present invention also concerns the use of a therapeutically or prophylactically effective amount of one or more of Sema3A antagonists of the present invention for reducing retinal vascular hyperpermeability in a subject. In an embodiment, the use is for the prevention or treatment of non-proliferative diabetic retinopathy. In another embodiment, the use is for the prevention or treatment of macular edema. In an embodiment, the macular edema is diabetic macular edema. In an embodiment, the diabetic macular edema is substantially free of neovascularization (i.e., it is mainly non-proliferative). In a further embodiment, the edema is age-related macular degeneration. In another embodiment, the age-related macular edema is substantially free of neovascularization.

In an embodiment, the above mentioned subject suffers from early stages of diabetes. In an embodiment, the subject suffers from type 1 diabetes mellitus (T1DM). In another embodiment, the subject suffers from type 2 diabetes mellitus. In an embodiment, the subject's vision is normal (he/she is asymptomatic i.e., does not suffer from symptoms associated with macular edema of vascular hyperpermeability such as spotted or blurry vision). In another embodiment, the subject does not suffer from substantial pericytes loss. In an embodiment, the subject has been diagnosed with non-proliferative diabetic retinopathy or macular edema. In an embodiment, the subject suffers from retinal swelling or retinal vascular hyperpermeability. In a specific embodiment, the subject is suffering from blood retinal barrier swelling.

In an embodiment, the Sema3A antagonist is administered prior to the onset of substantial macular edema. In another embodiment, the Sema3A antagonist is administered prior to the onset of blurry or spotted vision. In another embodiment, the Sema3A antagonist is administered prior to VEGF inducement (i.e., prior to an increase in VEGF expression). In another embodiment, the Sema3A antagonist of the present invention is administered in combination with one or more other drugs used for the prevention and/or treatment of macular edema and/or diabetes. Non-limiting examples of drugs used for the treatment of macular edema comprises bevacizumab (Avastin™), Ranibuzimad (Lucentis™), aflibercept (Eylea™) and corticosteroids. The present invention also concern compositions comprising a Sema3a antagonist alone or in combination with one or more drugs used for the treatment of macular edema and diabetic retinopathy.

Having demonstrated that increased Sema3A activity is associated with the BRB leakage and retinal vascular hyperpermeability, the invention relates to the use of Sema3A as a target in screening assays used to identify compounds that are useful for the prevention or treatment of retinal vascular hyperpermeability (e.g., non-proliferative diabetic retinopathy and macular edema), said method comprising determining whether:
    (a) the level of expression of a Sema3A nucleic acid or encoded polypeptide;
    (b) the level of Sema3A activity;
    (c) the level of a molecule generated by a Sema3A activity; or
    (d) any combination of (a) to (c);
is decreased in the presence of a test compound relative to in the absence of the test compound; wherein the decrease is indicative that the test compound is potentially useful for the prevention and treatment of retinal vascular hyperpermeability. In an embodiment, the above-mentioned method is an in vitro method. In an embodiment, the Sema3A activity is its binding to the Nrp-1 receptor. In a further embodiment, the Sema3A activity is the increased vascular permeability.

The present invention also relates to a method of identifying or characterizing a compound for preventing or treating retinal vascular hyperpermeability comprising:
    a) contacting a test compound with a cell comprising a first nucleic acid comprising a transcriptionally regulatory element (e.g., endogenous promoter or fragment thereof) normally associated with a Sema3A gene, operably-linked to a second nucleic acid comprising a reporter gene capable of encoding a reporter protein; and
    b) determining whether the reporter gene expression or reporter activity is decreased in the presence of the test compound;
wherein a decrease in the reporter gene expression or reporter gene activity is indicative that the test compound may be used for decreasing vascular hyperpermeability (e.g., treating or preventing non-proliferative diabetic retinopathy and macular edema).

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 2 shows that neuronal Sema3A is upregulated in the early phases of STZ-induced diabetes and its expression is geographically consistent with a role in macular edema. (a) Streptozotocin (STZ) was administered to ~6 week-old C57BL/6J mice and glycemia monitored according to the scheme; a mouse with non-fasted glycemia higher than 17 mM (300 mg/dL) was considered diabetic. (b) At 4 weeks after induction of diabetes, retinal Sema3A mRNA levels rose more than 2-fold in STZ treated mice when compared to vehicle-injected controls (P=0.0045, n=5), ~3-fold at 8 weeks (P=0.0011, n=8), 4-fold at 12 weeks (P=0.00846, n=4) and ~2.5 fold at 14 weeks (P=0.0334, n=3). Conversely, VEGF levels remained unchanged until 14 weeks where they rose by ~3-fold (P=0.0253, n=3). (c) Pericyte-specific staining of smooth muscle actin (SMA) in STZ- and vehicle-treated mice showing that Sema3A expression preceded pericyte loss. (d) Pathologically elevated blood glucose ~30 mM (p<0.0001, for both time points) at both 4 and 8 weeks of diabetes, STZ-treated mice. (e) At 8 weeks, tight junction (TJ) component occludin mRNA levels remained unchanged, whereas claudin-5 decreased by 38.6% (p<0.01). (f) Immunohistochemistry of Sema3A on retinal cryosections and co-localization with the retinal ganglion cell (RGC) marker pIII-tubulin, of the ganglion cell layer (GCL) and inner-nuclear layer (INL). (g) Laser-capture micro-dissection of retinal layers from normal and diabetic mice. (h) Quantitative RT-PCR for Sema3A on retinal layers of normal and diabetic mice.

FIG. 3 shows that the retinal barrier function is compromised by Sema3A. (a) Intravitreal injection of Sema3A resulted in a ~2-fold increase (p<0.01) in retinal vascular permeability (VP) as determined by Evans Blue (EB) permeation; a similar increase was observed with intravitreal administration of VEGF (p<0.05) and with a combination of both Sema3A and VEGF (p<0.01). (b) Confocal images of retinal sections injected with vehicle, VEGF and SEMA3A, showing the representative pattern of increased EB leakage. (c) Trans-endothelial resistance measured by ECIS demonstrates that Sema3A effectively reduces endothelial barrier function. (d) Western blot (WB) analysis of Human Retinal Microvascular Endothelial Cells (HRMECs); treatment with either Sema3A or VEGF lead to robust phosphorylation of Src at Tyr416; FAK was phosphorylated on Tyr576 and 577 (sites for Src-kinases); the adherence junction protein VE-cadherin became phosphorylated respectively on tyrosine-731 (pY731), site associated with increased VP; an additive or enhanced effect was not observed when simulation was performed with a combination of Sema3A and VEGF, suggesting action via redundant pathways. (e) Schematic representation of Sema3A signaling leading to VE-cadherin phosphorylation and tight junctions loosening. (f) Confocal microscopy of Sema3A-treated HRMECs revealed formation of vascular retraction fibers as determined by VE-cadherin and phalloidin staining (white arrows; FIG. 3f); retraction was similar to that with VEGF alone or with a combination of VEGF and Sema3A. (g) Flatmounted retinas injected with Sema3A or VEGF showed higher VE-cadherin phosphorylation at Y731 (white arrows) than vehicle-injected retinas in colocalization with retinal vessels—lectin stain—. (h) Retinal flatmounts from STZ-injected and vehicle-injected mice. (i) Cell death and apoptosis by caspase 3 assessment following Sema3A treatment (100-200 µM).

FIG. 6 shows human Sema3A precursor protein sequence (SEQ ID NO:1). This sequence is further processed into mature form. Residues 1-20 correspond to the signal peptide;

FIG. 7 shows human soluble Neuropilin-1 (Nrp-1) receptor protein sequence (GenBank Acc. No. AAH07737.1-SEQ ID NO:2) and FIG. 8 shows an alignment between rat (SEQ ID NO:15, Access. Nos. EDL96784, NP 659566), human (SEQ ID NO: 12, Accession No. NP_003864) and mouse (SEQ ID NO: 14, Accession No. ACCESSION NP_032763) Nrp-1 together with signal domain, Sema3a binding domains a1a2, VEGF binding domains b1b2, domain C, cytoplasmic domain and transmembrane domain.

DESCRIPTION OF ILLUSTRATIVE EMBODIMENTS

Figure 1:
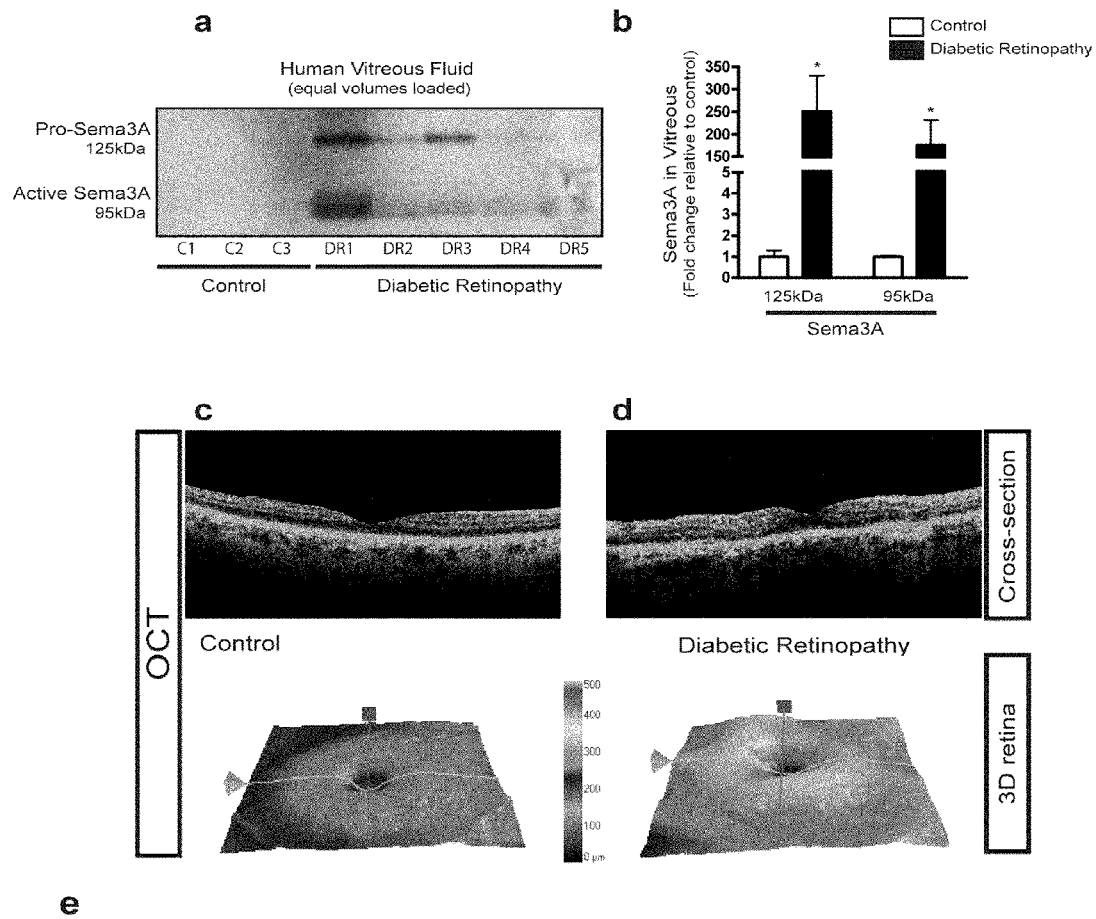
FIG. 1 shows elevated Sema3A levels in the vitreous of human T1 DM patients suffering from diabetic retinopathy. (a) Western blot (Wb) analysis revealed that both pro-(~125 kDa) and active (~95 kDa) forms of Sema3A were robustly induced in patients affected by Type 1 Diabetes Mellitus. (b) Wb quantification, ~125 kDa Sema3A signal was ~250-fold higher in DR relative to controls (p<0.05); ~95 kDa Sema3A signal was ~175-fold in DR patients (p<0.05). (c,d) Optical Coherence Tomography (OCT) revealed significant retinal swelling, mostly in the macular and peri-macular zones. (e) Detailed patient characteristics.

The deterioration of the blood retinal barrier and consequent macular edema is a cardinal manifestation of diabetic retinopathy (DR) and the clinical feature most closely associated with loss of sight. While macular edema affects over 25% of patients suffering from diabetes, currently available treatment modalities such as locally administered corticosteroids and recently approved anti-VEGF therapies, present several drawbacks. Here Applicant provides the first evidence from both human and animal studies for the role of the classical neuronal guidance cue Semaphorin3A in instigating pathological macular vascular permeability in type I diabetes. While classically associated with embryogenesis and neuronal and vascular patterning, investigation of the dynamics of expression reveal that Semaphorin3A is also induced in the early hyperglycemic phases of diabetes within the neuronal retina and precipitates initial breakdown of endothelial barrier function. Using the streptozotocin mouse model as a proxy for human diabetic retinopathy, Applicant demonstrates by a series of orthologous approaches (gene silencing or treatment with soluble Neuropilin-1 employed as a Semaphorin3A trap), that neutralization of Semaphorin3A efficiently prevents retinal vascular leakage. The increase in permeability provoked by Semaphorin3A is mediated through its cognate receptor, Neuropilin-1. Conditional knockout of Neuropilin-1 in Tg$^{Cre-Esr1}$Nrp1$^{flox/flox}$ mice diminishes Semaphorin3A-induced ocular permeability. The present findings identify a new therapeutic target for the prevention or treatment of non-proliferative retinopathy, macular edema and in particular DME.

Definitions

As used herein, the term Sema3A refers to Sema3A (e.g., HGNC: 10723; Entrez Gene: 10371; Ensembl: ENSG00000075213; OMIM: 603961; UniProtKB: Q14563;-FIG. 6, SEQ ID NO:1) and its functional isoforms, and allelic/polymorphic variants. Sema3A encodes a protein with an Ig-like C2-type (immunoglobulin-like) domain, a PSI domain and a Sema domain. This secreted protein can function as either a chemorepulsive agent, inhibiting axonal outgrowth and neovascularization, or as a chemoattractive agent, stimulating the growth of apical dendrites. It is expressed in various tissues including stressed retinal ganglion neurons.

"Sema3A-mediated cellular activity" refers in general to the physiological or pathological events in which Sema3A has a substantial role. Non-limiting examples of such activities include i) deterioration of the blood retinal barrier; ii) increased vascular permeability (i.e., hyperpermeability); iii) inhibition of VEGF-induced neovascularization at a hypoxic site (anti angiogenic effect); and modulation of axonal growth (e.g., inducement of growth cone collapse). Sema3A binds to the Neuropilin-1 receptor (Nrp-1).

As used herein, the term "Neuropilin-1 receptor" or "Nrp-1" receptor refers to neuropilin-1 and its isoforms, and allelic/polymorphic variants involved in Sema3A binding and signal transduction (e.g., HGNC: 8004; Entrez Gene: 8829; Ensembl: ENSG00000099250; OMIM: 602069; and UniProtKB: O14786; FIG. 7, SEQ ID NO:2, SEQ ID NO:12). The basic structure of neuropilin-1 comprises 5 domains: three extracellular domains (a1a2, b1b2 and c), a transmembrane domain and a cytoplasmic domain (See FIG. 8 and SEQ ID NO:12). The a1a2 (SEQ ID NO:13) domain is homologous to complement sedxw234weqqcomponents C1r and C1s (CUB) which generally contain 4 cysteine residues forming disulfide bridges. This domain binds Sema3A. There exists several splice variants isoforms and soluble forms of neuropilin-1 which are all encompassed by the present invention.

Figure 8:
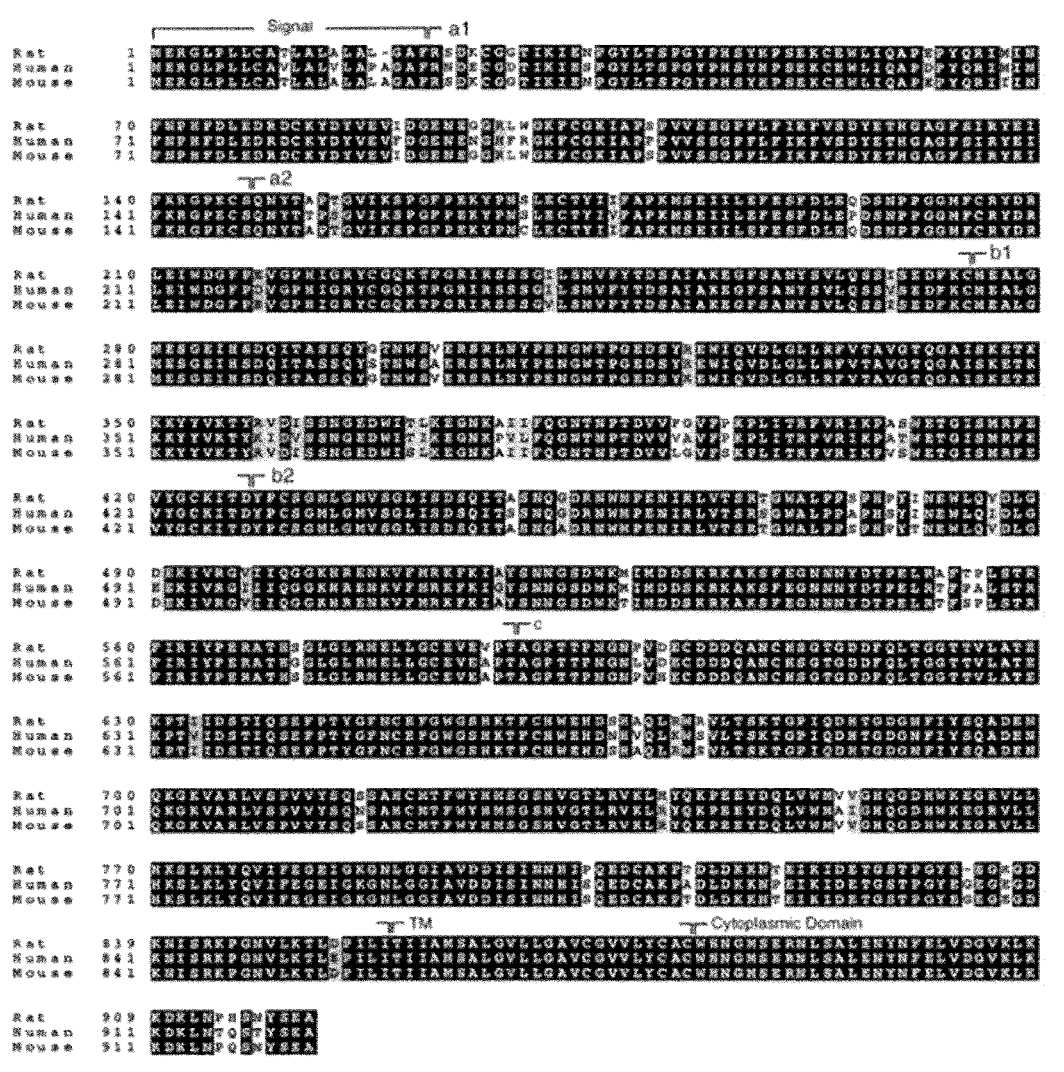

As used herein, "functional fragment" or "functional variant" (e.g., a functional fragment of soluble Nrp-1 polypeptide or polynucleotide of the present invention) refers to a molecule which retains the same activity as the original molecule but which differs by any modifications, and/or amino acid/nucleotide substitutions, deletions or additions (e.g., fusion with another polypeptide). Modifications can occur anywhere including the polypeptide/polynucleotide backbone (e.g., the amino acid sequence, the amino acid side chains and the amino or carboxy termini). Such substitutions, deletions or additions may involve one or more amino acids or in the case of polynucleotide, one or more nucleotide. The substitutions are preferably conservative, i.e., an amino acid is replaced by another amino acid having similar physico-chemical properties (size, hydrophobicity, charge/polarity, etc.) as well known by those of ordinary skill in the art. Functional fragments of the soluble Nrp-1 (SEQ ID NO:2) receptor include a fragment or a portion of a soluble Nrp-1 polypeptide (e.g., the a1a2 domain, SEQ ID NO:13) or a fragment or a portion of a homologue or allelic variant of a Nrp-1 which retains inhibiting activity, i.e., binds to Sema3A and inhibits the transduction of Sema3A-mediated cellular activity. In a particular embodiment, the Sema-3A-mediated cellular activity is vascular hyperpermeability. In an embodiment, the Npr-1 polypeptide is at least 80, 85, 88, 90, 95, 98 or 99% identical to SEQ ID NO:2. In an embodiment, the Npr-1 polypeptide is at least 80, 85, 88, 90, 95, 98 or 99% identical to domains a1, a2, IA and/or b2 of Npr-1 as depicted in FIG. 8. In an embodiment, the Npr-1 is a functional variant which includes variations in amino acids which are not conserved between rat, mouse and human Nrp-1 as depicted in FIG. 8. Preferably, the Npr-1 polypeptide/polynucleotide or fragment thereof is human.

In further embodiments, polypeptides and nucleic acids which are substantially identical to those noted herein may be utilized in the context of the present invention.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid/polynucleotide sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90%, 95%, 98% or 99% identical. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs 1-14.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 98%, or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, J. Mol. Biol. 215:403-10 (using the published default settings). Software for performing BLAST analysis may be available through the National Center for Biotechnology Information (through the internet at www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH. For example, in an embodiment, the Sema3A antagonist is an antisense/RNAi or shRNA that hybridizes to an Nrp-1 nucleic acid sequence (preferably a human sequence).

As used herein the term "treating" or "treatment" in reference to macular edema and/or non-proliferative retinopathy is meant to refer to a reduction/improvement in one or more symptom of macular edema and/or non-proliferative diabetic retinopathy including but not limited to vision impairment (e.g., blind spots, spotty or blurry vision), retinal swelling, macular edema, vascular hyperpermeability; blood retinal barrier integrity, retinal thickening, pericytes loss and/or presence of circinate rings of hard exudates.

As used herein the term "preventing" or "prevention" in reference to macular edema or vascular hypermeability is meant to refer to a reduction in the progression or a delayed onset of at least one of a vision impairment (e.g., blind spots, spotty or blurry vision), retinal swelling, macular edema, vascular swelling/leakage, blood retinal barrier integrity, retinal thickening, pericytes loss and/or presence of circinate rings of hard exudates.

As used herein, the term vascular hyperpermeability refers to an abnormal increase of the permeability of blood vessels and/or capillaries compared to normal conditions e.g., in non-diabetic patients or patients not suffering from any form of macular edema or retinal swelling. Vascular hyperpermeability may be acute (transient) or chronic. As a result of vascular hyperpermeability fluid moves from the blood stream past the blood vessels walls, thereby forming an area of edema. In the context of the present invention, vascular hyperpermeability include swelling (e.g., retinal swelling) and abnormal leakage of the blood vessels including through the blood retinal barrier.

As used herein the term "Sema3A inhibitor" or "Sema3A antagonist" refers to an agent able to reduce or block Sema3A-mediated cell signaling. Non-limiting examples include an agent which reduces or blocks the expression (transcription or translation) of Sema3A, an agent able to reduce or block Sema3A secretion or an agent able to reduce or block Sema3A binding to its receptor Nrp-1 and an agent which reduce or block (transcription or translation) of Npr-1. Without being so limited, the agent can be natural or synthetic and can be a protein/polypeptide such as but not limited to an antibody that specifically binds to Sema3A or Nrp-1 receptor; a soluble Nrp-1 polypeptide or fragment thereof, a peptide, a small molecule, a nucleotide such as but not limited to an antisense or a shRNA specific to Sema3A nucleic acid sequence encoding a Sema3A protein (e.g., SEQ ID NO:1) or Npr-1 nucleic acid sequence (Gene ID 8829 (human), Gene ID 18186 (mus musculus) or GeneID 246331 (rattus Norvegicus) encoding a Npr-1 protein (e.g., SEQ ID NO:2 or 12). In an embodiment, the agent is able to prevent Sema3A-mediated cell signaling without substantially reducing VEGF binding to the Nrp-1 receptor and thus VEGF-mediated cellular signaling.

Methods, compositions, uses and packages of the present invention are particularly useful for mammals and preferably humans. In a particular embodiment, the subject to which the Sema3A inhibitor of the present invention is administered suffers from diabetes. In another embodiment, the subject is at risk of suffering from diabetes. In an embodiment, the diabetes is Type 1 diabetes mellitus (T1DM). In an embodiment, the subject has been diagnosed with macular edema or is at risk of suffering from macular edema. In an embodiment, the macular edema is diabetic macular edema. In an embodiment the macular edema is diffuse macular edema. In another embodiment, the macular edema is focal macular edema. In an embodiment, the subject suffers from non-proliferative retinopathy (i.e., pathological neovascularization is absent or substantially low at the time the Sema3A inhibitor is administered). In an embodiment, the subject is suffering from early stage diabetes. In a related embodiment, the subject has an increased blood glucose level compared to a healthy subject. In yet another embodiment, the subject does not suffer from a substantial loss of pericytes. In yet another embodiment, the diabetic subject suffers from retinal swelling.

As used herein, the expression "early stage diabetes" or the like means that the subject is still at an early stage of diabetes e.g., stages 1-4, preferably, 1-3. Stage 1 is characterized by compensation: insulin secretion increases to maintain normoglycemia in the face of insulin resistance and/or decreasing β-cell mass. This stage is characterized by maintenance of differentiated function with intact acute glucose-stimulated insulin secretion (GSIS). Stage 2 occurs when glucose levels start to rise, reaching! 5.0-6.5 mmol/l; this is a stable state of β-cell adaptation with loss of β-cell mass and disruption of function as evidenced by diminished GSIS and ι β-cell dedifferentiation. Stage 3 is a transient unstable period of early decompensation in which glucose levels rise relatively rapidly to the frank diabetes of stage 4, which is characterized as stable decompensation with more severe β-cell dedifferentiation. Finally, stage 5 is characterized by severe decompensation representing a profound reduction in β-cell mass with progression to ketosis. Movement across stages 1-4 can be in either direction. For example, individuals with treated type 2 diabetes can move from stage 4 to stage 1 or stage 2. For type 1 diabetes, as remission develops, progression from stage 4 to stage 2 is typically found (see Diabetes 53 (Suppl. 3):S16-S210, 2004, which is incorporated herein by reference in its entirety)

As used herein "pharmaceutically acceptable carrier" or "excipient" includes any and all solvents, dispersion media, coatings, antibacterial and antifungal agents, physiological media, and the like that are physiologically compatible. In embodiments the carrier is suitable for ocular administration. Pharmaceutically acceptable carriers include sterile aqueous solutions or dispersions and sterile powders for the extemporaneous preparation of sterile injectable solutions or dispersion. The use of such media and agents, such as for ocular application, is well known in the art. Except insofar as any conventional media or agent is incompatible with the compounds of the invention, use thereof in the compositions of the invention is contemplated. Supplementary active compounds can also be incorporated into the compositions.

Methods of Treating or Preventing Vascular Hyperpermeability

In a first aspect, the present invention concerns a therapeutic approach to the inhibition of vascular hyperpermeability and the formation of macular edema in subjects by administering a compound that specifically inhibit Sema3A-mediated cellular activity. Sema3A-mediated cellular activity can be inhibited by a number of approaches. Inhibition of Sema3A cellular activity may be done directly by reducing Sema3A nucleic acid or protein expression or by inhibiting the binding of Sema3A to its associated receptor, Nrp-1. Inhibition of Sema3A activity may also be achieved indirectly by targeting one of Sema3A known downstream effectors (e.g., by targeting the Nrp-1 receptor) involved in Sema3A-induced vascular hyperpermeability. Non-limiting examples of approaches for inhibiting Sema3A-mediated cellular activity include i) antibodies specific for Sema3A; ii) antibodies specific for Nrp-1 (i.e., competing with Sema3A binding to the receptor); ii) by antisense and RNAi methods for reducing Sema3A expression and iv) by providing a soluble Nrp-1 receptor or fragment thereof, acting as a functional Sema3A trap.

Inhibition of Sema3A-Mediated Cellular Activity a. Antibodies

In a particular aspect of the present invention, Sema3A cellular activity (e.g., Sema3A-mediated-vascular hyperpermeability) can be inhibited by using Sema3A antibodies. In a particular embodiment, these antibodies bind to the portion of Sema3A which interacts with its cognate receptor, Nrp-1, thereby preventing Sema3A-mediated cellular signaling[41].

Alternatively, antibodies directly targeting the Nrp-1 receptor, which block the binding of Sema3A binding to Nrp-1 may also be used. In a particular aspect of the present invention, antibodies targeting Nrp-1 block Sema3A binding to the receptor but do not substantially interfere with VEGF binding to Nrp-1. In an embodiment, the Nrp-1 antibody binds to the a1a2 (A) domain of the Nrp-1 polypeptide.

As used herein, the term "Sema3A antibody" refers to an antibody that specifically binds to (interacts with) a Sema3A protein and displays no substantial binding to other naturally occurring proteins other than the ones sharing the same antigenic determinants as the Sema3A protein. Similarly, the term "Nrp-1 antibody" refers to an antibody that specifically binds to (interacts with) a Nrp-1 protein and displays no substantial binding to other naturally occurring proteins other than the ones sharing the same antigenic determinants as the Nrp-1 protein. Sema3A/Nrp-1 antibodies include polyclonal, monoclonal, humanized as well as chimeric antibodies. The term antibody or immunoglobulin is used in the broadest sense, and covers monoclonal antibodies (including full length monoclonal antibodies), polyclonal antibodies, multispecific antibodies and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions (VH, VH-VH), anticalins, PepBodies™, antibody-T-cell epitope fusions (Troybodies) or Peptibodies.

Anti-human sem3A/Nrp-1 antibodies have been previously prepared[43] and are also commercially available from various sources including Santa Cruz.

In general, techniques for preparing antibodies (including monoclonal antibodies and hybridomas) and for detecting antigens using antibodies are well known in the art and various protocols are well known and available.

b. Soluble Nrp-1 Receptor or Fragment Thereof

In accordance with the present invention, soluble Nrp-1 receptor (UniprotKB/Swiss prot 014786, isoform 2) or a functional fragment thereof may be used to reduce Sema3A induced vascular hyperpermeability. In a particular embodiment, the soluble Nrp-1 receptor functional fragment is a fragment which binds to Sema3A but not to VEGF. For example the functional fragment may comprise the a1a2 domain which binds to Sema3A but not to VEGF.

Inhibition of Sem3A Expression

Various approaches are available for decreasing Sema3A expression and thus Sema3A induced vascular hyperpermeability in the retina which contributes to macular edema. Non-limiting example includes the use of small hairpin shRNA (RNAi), antisense, ribozymes, TAL effectors targeting the Sema3A promoter or the like.

Expression of shRNAs in cells can be obtained by delivery of plasmids or through viral (e.g., lentiviral vector) or bacterial vectors. In a particular embodiment, the shRNAs which may be used in accordance with the present invention have the following sequences.

TABLE 1 sequences of shRNAs against Sema3A.

| ShRNA | target | Mature Antisense Sequence | SEQ ID NO: |
|---|---|---|---|
| TRCN0000058138 | Human Sema3A | AAATCCTTGAT ATTAACCAGG | 3 |
| TRCN0000058139 | Human Sema3A | TTTCCCGTAAA TATCACACCG | 4 |
| TRCN0000058142 | Human Sema3A | TTGAAACTACT TTAAGAACGG | 5 |
| TRCN0000058140 | Human Sema3A | AAATTAGCACA TTCTTTCAGG | 6 |
| TRCN0000067328 | Mouse Sema3A | AAATTGCCAAT ATACCAAGGC | 7 |
| TRCN0000067331 | Mouse Sema3A | AATGAGCTGCA TGAAGTCTCG | 8 |
| TRCN0000067330 | Mouse Sema3A | AAATTGGCACA TTCTTTCAGG | 9 |
| TRCN0000067329 | Mouse Sema3A | TTCATTAGGAA TACATCCTGC | 10 |
| TRCN0000067332 | Mouse Sema3A | TTATTTATAGG AAACACTGGG | 11 |

Therefore, in alternative embodiments, the invention provides antisense, shRNA molecules and ribozymes for exogenous administration to effect the degradation and/or inhibition of the translation of mRNA of interest. Preferably, the antisense, shRNA molecules and ribozymes target human Sema3A. Examples of therapeutic antisense oligonucleotide applications include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. No. 5,276,019 and U.S. Pat. No. 5,264,423; BioWorld Today, Apr. 29, 1994, p. 3.

Preferably, in antisense molecules, there is a sufficient degree of complementarity to the mRNA of interest to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as Shc inhibitors of the invention is disclosed in U.S. Pat. No. 5,932,435.

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991, Science 254:1497 and U.S. Pat. No. 5,539,082). The phosphodiester bonds may be substituted with structures which are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, $SCH_3$, F, OCN, $O(CH_2)_n$ $NH_2$ or $O(CH_2)_n$ $CH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

In a further embodiment, expression of a nucleic acid encoding a polypeptide of interest (Sema3A or Nrp-1), or a fragment thereof, may be inhibited or prevented using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example published US patent applications 20020173478 (Gewirtz; published Nov. 21, 2002) and 20020132788 (Lewis et al.; published Nov. 7, 2002). Reagents and kits for performing RNAi are available commercially from for example Ambion Inc. (Austin, Tex., USA) and New England Biolabs Inc. (Beverly, Mass., USA).

The initial agent for RNAi in some systems is a dsRNA molecule corresponding to a target nucleic acid. The dsRNA (e.g., shRNA) is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced.

RNAi may be effected by the introduction of suitable in vitro synthesized siRNA (shRNAs) or siRNA-like molecules into cells. RNAi may for example be performed using chemically-synthesized RNA. Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using E. coli RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods and various methods for introducing such vectors into cells, either in vitro or in vivo (e.g. gene therapy) are known in the art.

Accordingly, in an embodiment expression of a nucleic acid encoding a polypeptide of interest (Sema3A or Nrp-1), or a fragment thereof, may be inhibited by introducing into or generating within a cell an siRNA or siRNA-like molecule corresponding to a nucleic acid encoding a polypeptide of interest (e.g. myostatin), or a fragment thereof, or to an nucleic acid homologous thereto. "siRNA-like molecule" refers to a nucleic acid molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a nucleic acid encoding a polypeptide of interest, or a fragment or variant (or a fragment of a variant) thereof. Such a variant is capable of encoding a protein having activity similar to the polypeptide of interest.

A variety of viral vectors can be used to obtain shRNA/RNAi expression in cells including adeno-associated viruses (AAVs), adenoviruses, and lentiviruses. With adeno-associated viruses and adenoviruses, the genomes remain episomal. This is advantageous as insertional mutagenesis is avoided. It is disadvantageous in that the progeny of the cell will lose the virus quickly through cell division unless the cell divides very slowly. AAVs differ from adenoviruses in that the viral genes have been removed and they have diminished packing capacity. Lentiviruses integrate into sections of transcriptionally active chromatin and are thus passed on to progeny cells. With this approach there is increased risk of insertional mutagenesis; however, the risk can be reduced by using an integrase-deficient lentivirus.

Pharmaceutical Compositions

The Sema3A inhibitors of the present invention can be administered to a human subject by themselves or in pharmaceutical compositions where they are mixed with suitable carriers or excipient(s) at doses to treat or prevent vascular hyperpermeabilty, non-proliferative retinopathy, retinal swelling or macular edema and associated symptoms. Mixtures of these compounds can also be administered to the subject as a simple mixture or in suitable formulated pharmaceutical compositions. A therapeutically effective dose further refers to that amount of the compound or compounds sufficient to result in the prevention or treatment of macular edema and/or associated symptoms (spotted or blurry vision, Sema3A-associated hyperpermeability, edema, retinal swelling, and/or blood retinal barrier leakage). Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include systemic, oral and ocular (eye drops or intraocular injections). Preferred routes of administration comprise eye drops and intraocular injections. The formulations may also be in the form of sustained release formulations.

Furthermore, one may administer the drug in a targeted drug delivery system, for example, in a liposome coated with endothelial or cell-specific antibody.

Composition/Formulation

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents of the invention may be formulated in aqueous solutions, preferably in physiologically compatible buffers such as Hanks's solution, Ringer's solution, or physiological saline buffer.

For ocular administration, the compounds can be formulated readily by combining the active compounds with pharmaceutically acceptable carriers suitable for ocular administration well known in the art.

The compounds may be formulated for ocular administration e.g., eye drops or ocular injections bolus injection. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Alternatively, other delivery systems for pharmaceutical compounds may be employed. Liposomes and emulsions are well known examples of delivery vehicles or carriers for hydrophobic drugs.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

The effective dose of the compound inhibits the cellular signaling function of Sema3A sufficiently to reduce or prevent vascular hyperpermeability and blood retinal barrier leakage without causing significant adverse effects. Certain compounds which have such activity can be identified by in vitro assays that determine the dose-dependent inhibition of Sema3A inhibitors.

For any compound used in the method of the invention, the therapeutically effective dose can be estimated initially from cellular assays. For example, a dose can be formulated in cellular and animal models to achieve a circulating concentration range that includes the 1050 as determined in cellular assays (i e., the concentration of the test compound which achieves a half-maximal inhibition of the cellular signaling function of Sema3A, usually in response to inflammatory mediators such as II-1β or other activating stimulus such as hypoxia, ischemia, cellular stress, ER stress.

A therapeutically effective amount refers to that amount of the compound that results in amelioration of symptoms in a subject. Similarly, a prophylactically effective amount refers to the amount necessary to prevent or delay symptoms in a patient (e.g., Sema3A-induced vascular hyperpermeability, spotted and/or blurry vision, pericytes loss, macular edema, retinal swelling, blood retinal barrier leakage, etc.). Toxicity and therapeutic efficacy of such compounds can be determined by standard pharmaceutical procedures in cell cultures or experimental animals, e.g., determining the maximum tolerated dose (MTD) and the ED (effective dose for 50% maximal response). The dose ratio between toxic and therapeutic effects is the therapeutic index and it can be expressed as the ratio between MTD and ED50. Compounds which exhibit high therapeutic indices are preferred. The exact formulation, route of administration and dosage can be chosen by the individual physician in view of the patient's condition.

Dosage amount and interval may be adjusted individually to provide levels of the active compound which are sufficient to maintain the Sema3A modulating effects, or minimal effective concentration (MEC). The MEC will vary for each compound but can be estimated from in vitro data; e. g. the concentration necessary to achieve substantial inhibition of Sema3A expression or activity (e.g., binding to Nrp-1 receptor) Dosages necessary to achieve the MEC will depend on individual characteristics and route of administration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include the prevention and treatment of macular edema such as diabetic macular edema and age-related macular edema, retinal vascular hyperpermeability, blood retinal barrier leakage or the like.

Screening Assays

Having demonstrated that increased Sema3A activity is associated with the BRB leakage and retinal vascular hyperpermeability, the invention relates to the use of Sema3A as a target in screening assays used to identify compounds that are useful for the prevention or treatment retinal vascular hyperpermeability (e.g., non-proliferative diabetic retinopathy, macular edema, retinal swelling, etc.), said method comprising determining whether:

(a) the level of expression of a Sema3A nucleic acid or encoded polypeptide;
(b) the level of Sema3A activity;
(c) the level of a molecule generated by a Sema3A activity; or
(d) any combination of (a) to (c);
is decreased in the presence of a test compound relative to in the absence of said test compound; wherein said decrease is indicative that said test compound is potentially useful for the prevention and treatment of retinal vascular hyperpermeability. In an embodiment, the above-mentioned method is an in vitro method. In an embodiment, the Sema3A activity is its binding to the Nrp-1 receptor. In a further embodiment, the Sema3A activity is the increased vascular permeability.

In another embodiment of the invention, a reporter assay-based method of selecting agents which modulate Sema3A expression is provided. The method includes providing a cell comprising a nucleic acid sequence comprising a Sema3A transcriptional regulatory sequence operably-linked to a suitable reporter gene. The cell is then exposed to the agent suspected of affecting Sema3A expression (e.g., a test/candidate compound) and the transcription efficiency is measured by the activity of the reporter gene. The activity can then be compared to the activity of the reporter gene in cells unexposed to the agent in question. Suitable reporter genes include but are not limited to beta(β)-D-galactosidase, luciferase, chloramphenicol acetyltransferase and green fluorescent protein (GFP).

Accordingly, the present invention further provides a method of identifying or characterizing a compound for treating or preventing retinal vascular hyperpermeability, the method comprising: (a) contacting a test compound with a cell comprising a first nucleic acid comprising a transcriptionally regulatory element normally associated with a Sema3A gene (e.g., a promoter region naturally associated with a Sema3A gene), operably linked to a second nucleic acid comprising a reporter gene capable of encoding a reporter protein; and (b) determining whether reporter gene expression or reporter protein activity is decreased in the presence of said test compound, said decrease in reporter gene expression or reporter protein activity being an indication that said test compound may be used for treating or preventing retinal vascular hyperpermeability (such as retinal swelling in non-proliferative diabetic retinopathy or macular edema). In an embodiment, the above-mentioned method is an in vitro method.

The above-noted assays may be applied to a single test compound or to a plurality or "library" of such compounds (e.g., a combinatorial library). Any such compound may be utilized as lead compound and further modified to improve its therapeutic, prophylactic and/or pharmacological properties for the prevention and treatment of obesity and/or obesity-related hypertension.

Such assay systems may comprise a variety of means to enable and optimize useful assay conditions. Such means may include but are not limited to: suitable buffer solutions, for example, for the control of pH and ionic strength and to provide any necessary components for optimal Sema3A activity and stability (e.g., protease inhibitors), temperature control means for optimal Sema3A activity and or stability, and detection means to enable the detection of the Sema3A and Nrp-1 interaction. A variety of such detection means may be used, including but not limited to one or a combination of the following: radiolabelling (e.g., $^{32}P$, $^{14}C$, $^{3}H$), antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/streptavidin), and others.

The assay may be carried out in vitro utilizing a source of Sema3A which may comprise naturally isolated or recombinantly produced Sema3A, in preparations ranging from crude to pure. Recombinant Sema3A may be produced in a number of prokaryotic or eukaryotic expression systems, which are well known in the art (see for example Martin F. et al., 2001. *Immunogenetics* 53(4): 296-306) for the recombinant expression of Sema3A. Such assays may be performed in an array format. In certain embodiments, one or a plurality of the assay steps are automated.

A homolog, variant and/or fragment of Sema3A which retains activity (e.g., it binds to the Nrp-1 receptor) may also be used in the screening methods of the invention. Homologues include protein sequences, which are substantially identical to the amino acid sequence of full length Sema3A (e.g., FIG. 1), or matured fragment, sharing significant structural and functional homology with Sema3A. Variants include, but are not limited to, proteins or peptides, which differ from a Sema3A by any modifications, and/or amino acid substitutions, deletions or additions (e.g., fusion with another polypeptide). Modifications can occur anywhere including the polypeptide backbone, (i.e., the amino acid sequence), the amino acid side chains and the amino or carboxy termini. Such substitutions, deletions or additions may involve one or more amino acids. Fragments include a fragment or a portion of a Sema3A or a fragment or a portion of a homologue or variant of a Sema3A which retains Sema3A activity, i.e., binds to the Nrp-1 receptor and causes vascular hyperpermeabilisation.

Example 1

Material and Methods

Human Samples

Approval of human clinical protocol and informed consent form by Maisonneuve-Rosemont Hospital (HMR) ethics committee and recruitment of patients for local core vitreal biopsy sampling from patients afflicted with T1 DM.

Animals

All studies were performed according to the Association for Research in Vision and Ophthalmology (ARVO) Statement for the Use of Animals in Ophthalmic and Vision Research and were approved by the Animal Care Committee of the University of Montreal in agreement with the guidelines established by the Canadian Council on Animal Care. C57Bl/6 wild-type were purchased from The Jackson Laboratory. Tamoxifen-inducible (Tam-inducible) Cre mice (Ter$^{Cre-Esr}$1; no. 004682) and Neuropilin 1 floxed mice (Nrp1$^{tm2Ddg}$/J; no. 005247) were purchased from The Jackson Laboratory.

Streptozotocin (STZ) Mouse Model

C57BL/6J mice of 6- to 7-week were weighted and their baseline glycemia was measured (Accu-Chek, Roche). Mice were injected intraperitoneally with streptozotocin (Sigma-Alderich, St. Louis, Mo.) for 5 consecutive days at 55 mg/Kg. Age-matched controls were injected with buffer only. Glycemia was measured again a week after the last STZ injection and mice were considered diabetic if their non-fasted glycemia was higher than 17 mM (300 mg/dL).

Real-Time PCR Analysis

RNA was isolated using the GenElute™ Mammalian Total RNA Miniprep Kit (Sigma) and digested with DNase I to prevent amplification of genomic DNA. Reversed transcription was performed using M-MLV reverse transcriptase and gene expression analyzed using SybrGreen™ in an ABI Biosystems™ Real-Time PCR machine. β-actin was used as a reference gene.

Laser-Capture Microdissection

Eyes were enucleated from P14 pups in OIR (oxygen induced retinopathy) or normoxic littermates and flash-frozen in OCT. We then cut 12 μm sections using a Leica cryostat at −20° C. and air-dried for 10 min. We dissected retinal layers using a Zeiss Observer microscope equipped with a Palm MicroBeam™ device for laser-capture microdissection. We isolated mRNA from these sections and performed qPCRs as described above.

Western-Blotting

For assessment of retinal protein levels, we enucleated eyes at varying time points and rapidly dissected and homogeneized retinas. Protein concentrations were assessed by BCA assay (Sigma), and then 30 ug of protein analyzed for each condition by standard SDS-PAGE technique. Antibodies used for Western-blotting are: Nrp-1 (R&D Systems, #AF566), pVE-Cadherin (Invitrogen, #441145G), Src (Cell Signaling, #2108), pSRC (Cell Signaling, #2101), FAK (Cell Signaling, #3285), pFAK (Cell Signaling, #3281), b-Actin (Sigma, #A2228), Sema3A (Santa Cruz, #sc-1148 OR ABCAM #ab23393).

Immunohistochemistry

To localize protein expression, eyes were enucleated from mice and fixed in 4% paraformaldehyde at room temperature for 4 h at RT and incubated in 30% sucrose overnight and then frozen in OCT compound. We then embedded the whole eye in optimal cutting temperature compound at −20° C. and performed 12 um serial sections. We carried out immunohistochemistry experiments and visualized the sections with an epifluorescent microscope (Zeiss AxioImager™) or confocal microscope (Olympus confocal FV1000). Antibodies used for immunohistochemistry are: Sema3A (ABCAM #ab23393), Smooth Muscle Actin (SMA) (ABMCA, #ab7817) and βIII-tubulin (ECM). Secondary antibodies are Alexa 594 (Invitrogen, #A11005) and Alexa 488 (Invitrogen, #A11008).

For visualization of pan-retinal vasculature, flatmount retinas were stained with stained with fluoresceinated Isolectin B4 (Alexa Fluor 594-I21413, Molecular Probes) in 1 mM CaCl$_2$ in PBS for retinal vasculature. For assessment of vascular permeability (see Evans Blue—EB—permeation), we injected mice vitreally with Vehicle and VEGF, after 2 hours of EB injection, the eyes were harvested and retinas were dissected for flatmount or prepared for cryosections and visualization under a fluorescent microscope Preparation of Lentivirus We produced infectious lentiviral vectors by transfecting lentivector and packaging vectors into HEK293T cells (Invitrogen) as previously described[40]. Viral supernatants were concentrated by ultra-centrifugation (>500-fold) and titers determined by ELISA for viral p24 antigen using a commercial kit (Clonetech).

Soluble Recombinant NRP1 and Mouse Anti-VEGF

STZ treated diabetic C57BL/6J mice were intravitreally injected with rmNRP1 from plasmid (Mamluk et al., 2002[17]) or R&D Systems at 6 and 7 weeks after STZ administration. Specific mouse anti-VEGF was purchased from R&D Systems (AF-493-NA) and 1 µl was injected at 80 ug/mL. Retinal Evans blue permeation assay was performed at 8 weeks after STZ treatment as described above.

Statistical Analyses

Data are presented as mean±s.e.m. We used Student's T-test and ANOVA, where appropriate, to compare the different groups; a $P<0.05$ was considered statistically different.

Example 2

Sema3A is Elevated in the Vitreous of Human Patients Suffering from Diabetic Retinopathy In order to evaluate the potential role of Sema3A in mediating the edematous phenotype observed in DR, we first sought to determine the presence of this guidance cue in the vitreous of patients suffering from DME. Vitreous was recovered during standard vitroretinal surgery from 8 patients. Five samples were obtained from T1 DM patients suffering from DME and 3 from control patients (non-vascular pathology) undergoing surgery for macular hole (MH) or Epiretinal Membrane (ERM).

Western blot analysis revealed that both pro-($\sim$125 kDa) and active ($\sim$95 kDa) forms of Sema3A were robustly induced in patients affected by DME (FIG. 1a,b). Consistent with a prospective role in DME, ELISA-based detection of Sema3A revealed a significant increase in the vitreous of patients suffering from DME when compared to nonvascular ocular pathologies (control median 3.79 ng/ml [interquartile range {IQR}: 25%, 75%: 2.08 ng/ml, 5.58 ng/ml]; DME median 16.27 ng/ml [IQR: 25%, 75%: 5.770 ng/ml, 35.36 ng/ml]; p=0.0464) (Data not shown). Spectral-domain. Optical Coherence Tomography (OCT) was performed and three-dimensional (3D) maps were generated to evaluate the extent of retinal damage and edema. In contrast to controls sampled DME patients showed significant retinal swelling, specifically in the macular and peri-macular zones as shown in FIG. 1c,d. Detailed DME patient characteristics are presented in FIG. 1e.

These data provide the rational to explore the role of Sema3A in the context of diabetes-induced retinal vasculopathy.

Example 3

Neuronal Sema3A is Upregulated in the Early Phases of Streptozotocin-Induced Diabetes Given the elevated levels of Sema3A in the vitreous of DME patients, Applicant sought to elucidate the dynamics and pattern of Sema3A expression in a mouse model of type 1 diabetes mellitus (T1DM). Streptozotocin (STZ) was administered over 5 consecutive days to 6-week-old C57BL/6J mice, and glycemia was monitored according to the scheme depicted in FIG. 2a. Mice were considered diabetic if their non-fasted glycemia was higher than 17 mM (300 mg/dL).

As early as 4 weeks after induction of diabetes, retinal levels of Sema3A where over 2-fold higher in STZ treated mice when compared to vehicle injected controls (p=0.0045, n=5). These significantly higher retinal levels of Sema3A persisted at 8 weeks (Sema3A, 2.80±0.340; p=0.0011; VEGF, 1.236±0.193; p=0.266, n=8), 12 weeks (Sema3A, 4.07±0.798; p=0.00846; VEGF, 0.923±0.145; p=0.612, n=4), and 14 weeks (Sema3A, 2.44±0.593; p=0.0334; VEGF, 3.26±0.65; p=0.0253, n=3). Importantly, throughout early time points of disease (4-12 weeks), VEGF levels in STZ-treated mice remained at similar levels to that observed in vehicle treated congener mice as has been previously described [24] (FIG. 2b). At all analyzed time-points, STZ-treated mice showed pathologically elevated blood glucose levels of ~30 mM (FIG. 2d; p<0.0001 for both 8 and 4 weeks of diabetes). Importantly, the rise in expression of Sema3A was an early event and preceded pericyte loss as both STZ and vehicle-treated mice showed similar levels of smooth muscle actin (SMA, FIG. 2c). Similarly, expression levels of the tight junction components occludin and claudin-5 varied minimally at the early time of 8 weeks (FIG. 2e). Finally mice both STZ- and vehicle-treated mice showed no significant difference in transcript levels for pericyte markers platelet-derived growth factor receptor-b (Pdgfr-b; 1.477±0.364; p=0.219, n=11), NG2 proteoglycan (Ng2; 2.065±0.886; p=0.316, n=4), or alpha smooth muscle actin (a-Sma; 1.342±0.441; p=0.494, n=4).

Example 4

The Expression Pattern of Sema3A is Geographically Consistent with a Role in Diabetic Retinopathy Applicant next sought to determine the cellular source of Sema3A in the diabetic retina. Immunohistochemistry on retinal cryosections revealed that Sema3A was strongly expressed by retinal neurons of the ganglion cell layer (GCL and inner-nuclear layer (INL) (FIG. 2f,g). The most prominent expression was noted in retinal ganglion cells (RGCs) as demonstrated by co-localization with the RGC marker pIII-tubulin. Consistent with the retinal immuno-localization of Sema3A, laser-capture micro-dissection of retinal layers from normal and diabetic mice followed by quantitative RT-PCR pinpointed Sema3A to neurons in close proximity to vascular beds (FIG. 2h).

Example 5

Retinal Barrier Function is Compromised by Sema3A

Given the observed rise in retinal Sema3A levels in diabetes, Applicant proceeded to investigate the propensity of Sema3A to disrupt vascular barrier function. Intravitreal injection of Sema3A resulted in a ~2-fold increase (FIG. 3a; p<0.01) in retinal vascular permeability as determined by Evans Blue (EB) permeation. This increase was similar to that observed with intravtireal administration of VEGF (FIG. 3a; p<0.05) or a combination of both Sema3A and VEGF (FIG. 3a; p<0.01). FIG. 3b depicts confocal images of retinal sections injected with vehicle, VEGF and Sema3A, showing the representative increased pattern of EB leakage. To further examine the ability of Sema3A to compromise endothelial barrier function, Applicant carried out real-time analysis of trans-endothelial electric resistance. Treatment of an intact endothelial monolayer with Sema3A reduced barrier function in a magnitude similar, yet lower than VEGF in the first 6 hours following addition (FIG. 3c).

Applicant next ascertained that Sema3A activated signaling pathways known to promote vascular permeability. In this respect Applicant investigated, by Western blot analysis, the activation profiles of Src and focal adhesion kinase (FAK) known to transduce extracellular signals that provoke the loosening of endothelial cell tight junctions[25-28]. Stimulation of Human Retinal Microvascular Endothelial Cells (HRMECs) by either Sema3A or VEGF lead to robust phosphorylation of Src at Tyr416 in the activation loop of the kinase domain which is reported to enhance enzyme activity[29]. In turn, FAK was phosphorylated on Tyr576 and 577 (sites for Src-kinases). Ultimately, the tight junction proteins VE-cadherin became phosphorylated respectively on tyrosine-731 (site associated with increased vascular permeability[30-32]) (FIG. 3d). Consistent with the above data on retinal permeability (FIG. 3a), an additive or enhanced effect was not observed when simulation was performed with a combination of Sema3A and VEGF suggesting that both factors signal via redundant pathways (FIG. 3d). In accordance to VE-cadherin western blot analysis (FIG. 3d), flatmounted retinas injected with Sema3A or VEGF showed higher VE-cadherin phosphorylation at Y731 (arrows) than vehicle-injected retinas in co-localization with lectin stained retinal vessels (FIG. 3g). Similarly, retinal flatmounts from STZ-injected and vehicle-injected mice showed VE-cadherin phosphorylation colocalizing with retinal vessels (FIG. 3h).

Consistent with a role in disrupting barrier function, confocal microscopy of Sema3A-treated HRMECs revealed pronounced formation of vascular retraction fibers as determined by VE-cadherin and phalloidin staining (white arrows; FIG. 3f). The observed retraction was similar to that with VEGF alone or with a combination of VEGF and Sema3A. Importantly, at the doses employed in the instant study (100-200 uM) Sema3A did not induce cell death or apoptosis as determined by assessment of activation of caspase-3 (FIG. 3i). These data underscore the direct effect on retinal vascular permeability of Sema3A.

Example 6

Figure 4:
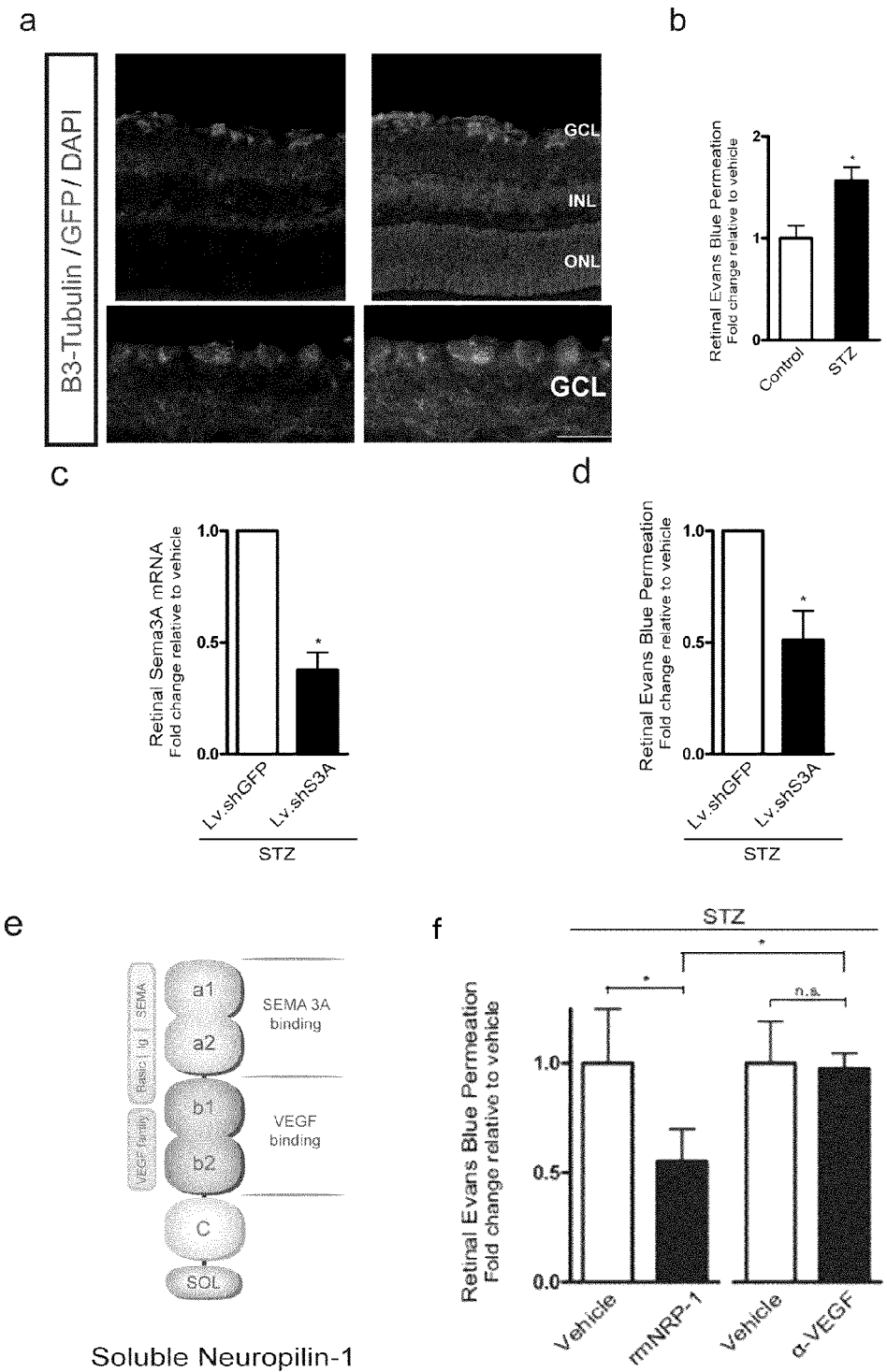
FIG. 4 shows that targeted silencing of neuron-derived Sema3A and intravitreal neutralization of Sema3A efficiently reduce vascular permeability in T1 DM. (a) Lentiviral vectors with a VSVG capsid exhibit high tropism for RGCs and cells of the ONL when delivered intravitreally, as depicted by Lv vector carrying GFP RNA.; Lv.shRNA against Sema3A was used to specifically block Sema3A production in RGCs or neurons of the INL in vivo. (b) While STZ-treated mice show a 56.8% increase in permeability (assessed by Evans Blue permeation, (p<0.05)), (c) a single intravitreal injection of Lv.shSema3A at 5 weeks of diabetes lead to a significant 62.3% reduction in retinal Sema3A expression (p<0.005) and (d) provoked a proportional 49.5% decrease in vascular leakage (p<0.05). (e) To neutralize vitreal Sema3A, we used recombinant (r) soluble Nrp-1 as a bivalent trap for both Sema3A and VEGF. Neuropilin-1 is a single-pass receptor with its extracellular domain subdivided into distinct sub-domains of which a1a2 bind semaphorin and b1b2 bind VEGF. (f) Intravitreal injection of rmNRP1 in STZ mice at weeks 6 and 7 after induction of diabetes lead to a 48.1% reduction in retinal permeability at week 8 of diabetes (P=0.012, n=6 (18 mice)). Conversely, injection of a neutralizing antibody against mouse VEGF was ineffective at reducing diabetes-induced retinal permeability at this stage of disease when compared to vehicle (P=0.7302, n=5 (14 mice)). Values expressed relative to vehicle injected retinas.

Inhibition of Neuron-Derived Sema3A Efficiently Reduces Vascular Permeability in T1 DM Recent studies demonstrate that retinal neurons may exert an important influence on the blood vessels that perfuse them[14,33-35]. In light of the robust expression of Sema3A in RGCs and the INL as well as its ability to promote vascular leakage, Applicant sought to inhibit production of this guidance cue directly in these cell populations. To specifically block Sema3A production in RGCs or neurons of the INL in vivo, lentiviral (Lv) vectors carrying a shRNA against Sema3A were generated (TTATTTATAGGAAACACTGGG-SEQ ID NO:11). These Lv vectors with a VSVG capsid exhibit high tropism for RGCs and cells of the ONL when delivered intravitreally1[14,35] (FIG. 4a). While STZ-treated mice show a 56.8% increase in permeability (FIG. 4b; p<0.05, n=4) a single intravitreal injection of Lv.shSema3A at 5 weeks of diabetes lead to a significant 62.3% reduction in retinal Sema3A expression (FIG. 4c; p<0.005, n=3) and provoked a proportional 49.5% decrease in vascular leakage (FIG. 4d; p<0.05, n=3). Hence, directly targeting Sema3A expression in neurons of the GCL and the INL where Sema3A was most abundantly expressed in diabetic mice (FIG. 2f-h) effectively reduced pathological vascular leakage.

Example 7

Intravitreal Neutralization of Sema3A Reduces Retinal Vascular Permeability

In order to neutralize vitreal Sema3A, we employed recombinant(r) soluble Nrp-1 as a bivalent trap for both Sema3A and VEGF. Neuropilin-1 is a single-pass receptor with its extracellular domain subdivided into distinct subdomains of which a1a2 binds semaphorin and b1b2 binds VEGF[36] (FIG. 4e). Intravitreal injection of rNrp-1 in STZ mice at week 6 and 7 after induction of diabetes lead to a 48.1% reduction in retinal permeability measured at week 8 of diabetes (FIG. 4f; p<0.05, n=5); a similar magnitude to that observed with gene silencing of Sema3A (FIG. 4d). Importantly, neutralization of VEGF with a neutralizing antibody for mouse VEGF$_{164}$ was not effective at reducing vascular permeability at this early stage of diabetes (vehicle vs anti-VEGF: 0.975±0.0707; P=0.7302 II rmNRP1 vs anti-mVEGF: P=0.035, n=5 distinct experiments with a total of 14 mice). This is likely attributed to the fact that VEGF is not increased in diabetic retinas at this early time point (8 weeks) while Sema3A is robustly induced (FIG. 2b). Together, these data indicate that neutralization of SEMA3A in the diabetic retina is an effective strategy to reduce vasogenic edema.

Example 8

Figure 5:
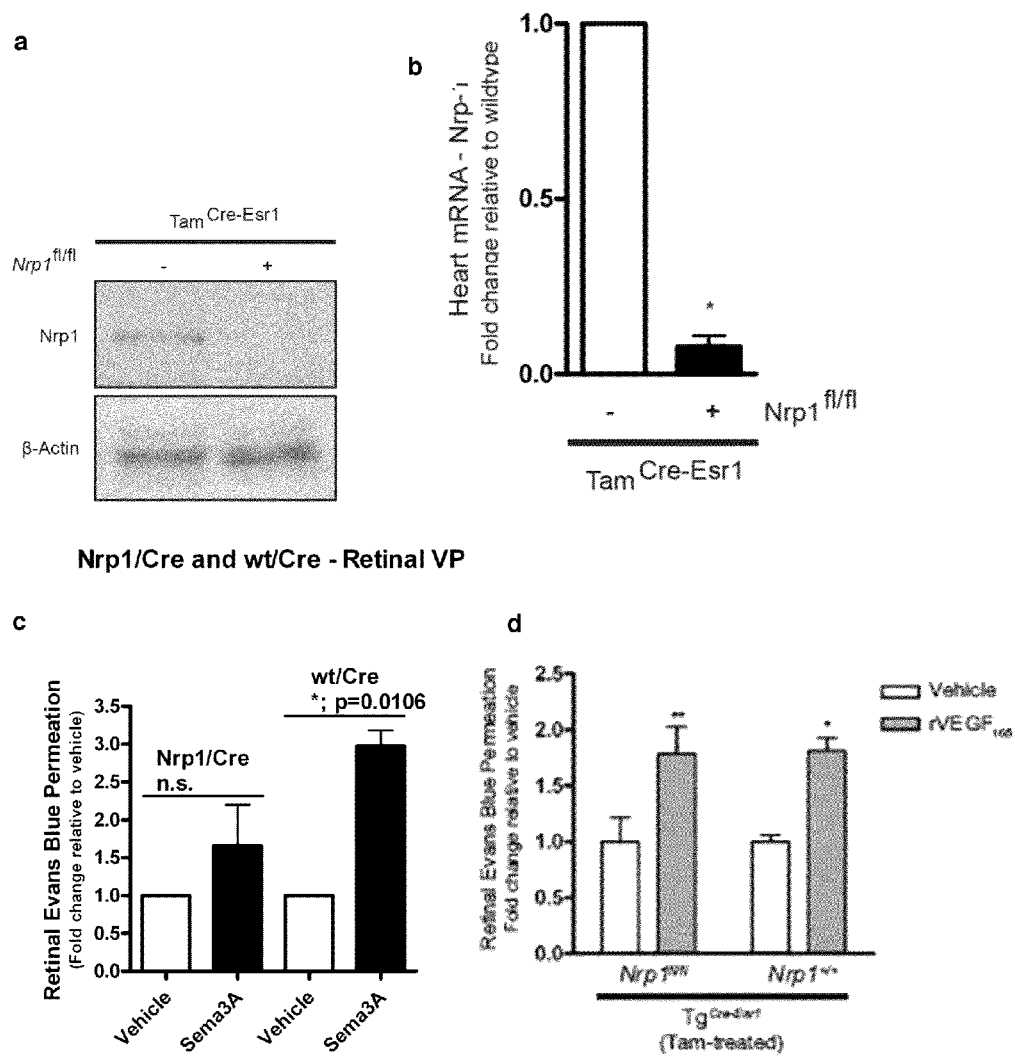
FIG. 5 shows that conditional knockout of Nrp-1 prevents Sema3A-induced retinal barrier function breakdown. Systemic administration of tamoxifen during a 5 day period effectively deleted Nrp-1 protein (a) and gene (b) expression. (c) In absence of NRP1, intravitreally administered Sema3A did not increase vascular leakage (P=0.36; n=7 (21 mice)), while Tam-treated TgCre-ESR1/Nrp1+/+ controls show 3-fold higher vascular leakage (P=0.00065; n=3 (9 mice)). (d) Conversely, disruption of Nrp1 did not influence VEGF-induced vascular retinal permeability (p=0.0024; n=3 (9 mice)), suggesting that VEGF-induced retinal vascular leakage is independent of NRP1 as previously reported.

Conditional Knockout of Nrp-1, Prevents Sema3A-Induced Retinal Barrier Function Breakdown In light of Nrp-1 being the receptor for Sema3A, Applicant sought to determine whether knockout of Nrp-1 protects against Sema3A-induced vascular permeability. Because systemic germline deletion of Nrp-1 is embryonic lethal [37-39], a whole-animal tamoxifen-inducible (Tam-inducible) Cre mouse (Tg$^{Cre-Esr1}$) was generated to induce Nrp-1 exon 2 deletion. To validate Cre recombination at the Nrp-1 locus and confirm disruption of Nrp-1 in vivo, Tg$^{Cre-Esr1}$; Nrp1$^{fl/fl}$ mice (iKO) and littermates were administered Tam or vehicle (Veh) at 6 weeks of age. Systemic administration of Tam over a period of 5 consecutive days lead to an efficient knockout of Nrp-1 in the vascular system as determined by Western blot (FIG. 5a) and qPCR (FIG. 5b: P=0.0012) and resulted in near complete absence of NRP1 in retinal vessels (assessed by immunofluorescence of retinal cryosections-data not shown). Importantly, Tam-treated iKO (Tam iKO) mice showed no difference in body weight, size or open-field activity compared with littermates from 4 through 20 weeks of age (data not shown). As expected, Tam treated TgCre-Esr1;Nrp1fl/fl mice with disrupted Nrp-1 were protected against Sema3a-induced vascular permeability following intravitreal injection of Sema3A (1.276±0.2901; P=0.36; n=7 distinct experiments with 21 mice) (FIG. 5c; while control Tam-treated TgCre-ESR1/Nrp1+/+ mice showed 3-fold higher vascular leakage in response to Sema3A (2.972±0.2045; P=0.00065; n=3 distinct experiments with a total of 9 mice). Conversely, disruption of Nrp1 did not influence VEGF-induced vascular retinal permeability (Tam-treated TgCre-Esr1/Nrp1fl/fl—

Vehicle vs VEGF: 1.814±0.1188, P=0.0024, n=3 distinct experiments with a total of 9 mice; Tam-treated TgCre-Esr1/Nrp1+/+—Vehicle vs VEGF: 1.783+0.2440; P=0.032, n=3 distinct experiments with a total of 9 mice) (FIG. 5d) indicating that VEGF-induced retinal vascular permeability does not require NRP1. This is in accordance with previous work. Efficiency of sh-mediated knockdown of Nrp1 was validated by qPCR (data not shown). Collectively, these data confirm that Sema3A-mediated inner-blood retinal barrier function breakdown is NRP1-dependent and validate NPR-1 as a good target for reducing Sema3A-mediated hyperpermeability and blood brain barrier leakage in macular edema.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. In the claims, the word "comprising" is used as an open-ended term, substantially equivalent to the phrase "including, but not limited to". The following examples are illustrative of various aspects of the invention, and do not limit the broad aspects of the invention as disclosed herein.

REFERENCES

1. Gilbert C, Rahi J, Eckstein M, O'Sullivan J, Foster A. Retinopathy of prematurity in middle-income countries. *Lancet*. Jul. 5, 1997; 350(9070):12-14.
2. Kempen J H, O'Colmain B J, Leske M C, et al. The prevalence of diabetic retinopathy among adults in the United States. *Arch Ophthalmol*. April 2004; 122(4):552-563.
3. Chen J, Smith L. Retinopathy of prematurity. *Angiogenesis*. Mar. 19, 2007; 10(2):133-140.
4. Cheung N. Diabetic retinopathy and systemic vascular complications. *Progress in Retinal and Eye Research*. Mar. 1, 2008; 27(2):161-176.
5. Smith L E. Through the eyes of a child: understanding retinopathy through ROP the Friedenwald lecture. *Invest Ophthalmol Vis Sci*. December 2008; 49(12):5177-5182.
6. Wang S, Park J K, Duh E J. Novel targets against retinal angiogenesis in diabetic retinopathy. *Curr Diab Rep*. August 2012; 12(4):355-363.
7. Antonetti D A, Klein R, Gardner T W. Diabetic retinopathy. *N Engl J Med. Mar.* 29, 2012; 366(13):1227-1239.
8. Moss S E, Klein R, Klein B E. The 14-year incidence of visual loss in a diabetic population. *Ophthalmology*. June 1998; 105(6):998-1003.
9. Silva P S, Cavallerano J D, Sun J K, Aiello L M, Aiello L P. Effect of systemic medications on onset and progression of diabetic retinopathy. *Nat Rev Endocrinol*. September 2010; 6(9):494-508.
10. Stahl A, Connor K M, Sapieha P, et al. The mouse retina as an angiogenesis model. *Invest Ophthalmol Vis Sci*. June 2010; 51(6):2813-2826.
11. Stewart M W. The expanding role of vascular endothelial growth factor inhibitors in ophthalmology. *Mayo Clin Proc*. January 2012; 87(1):77-88.
12. Sapieha P, Hamel D, Shao Z, et al. Proliferative retinopathies: angiogenesis that blinds. *Int J Biochem Cell Biol*. January 2010; 42(1):5-12.
13. Robinson G S, Ju M, Shih S C, et al. Nonvascular role for VEGF: VEGFR-1, 2 activity is critical for neural retinal development. *FASEB J*. May 2001; 15(7):1215-1217.
14. Joyal J-S, Sitaras N, Binet F, et al. Ischemic neurons prevent vascular regeneration of neural tissue by secreting semaphorin 3A. *Blood*. 2011; 117(22):6024-6035.
15. Lee P, Goishi K, Davidson A J, Mannix R, Zon L, Klagsbrun M. Neuropilin-1 is required for vascular development and is a mediator of VEGF-dependent angiogenesis in zebrafish. *Proc Natl Acad Sci USA. Aug.* 6, 2002; 99(16):10470-10475.
16. Gluzman-Poltorak Z, Cohen T, Shibuya M, Neufeld G. Vascular endothelial growth factor receptor-1 and neuropilin-2 form complexes. *J Biol Chem. Jun.* 1, 2001; 276(22):18688-18694.
17. Mamluk R, Gechtman Z, Kutcher M E, Gasiunas N, Gallagher J, Klagsbrun M. Neuropilin-1 binds vascular endothelial growth factor 165, placenta growth factor-2, and heparin via its b1b2 domain. *J Biol Chem*. Jul. 5, 2002; 277(27):24818-24825.
18. Miao H Q, Soker S, Feiner L, Alonso J L, Raper J A, Klagsbrun M. Neuropilin-1 mediates collapsin-1/semaphorin III inhibition of endothelial cell motility: functional competition of collapsin-1 and vascular endothelial growth factor-165. *J Cell Biol. Jul.* 12, 1999; 146(1):233-242.
19. Klagsbrun M, Eichmann A. A role for axon guidance receptors and ligands in blood vessel development and tumor angiogenesis. *Cytokine Growth Factor Rev*. August-October 2005; 16(4-5):535-548.
20. Klagsbrun M, Takashima S, Mamluk R. The role of neuropilin in vascular and tumor biology. *Adv Exp Med Biol*. 2002; 515:33-48.
21. Soker S, Miao H Q, Nomi M, Takashima S, Klagsbrun M. VEGF165 mediates formation of complexes containing VEGFR-2 and neuropilin-1 that enhance VEGF165-receptor binding. *J Cell Biochem*. 2002; 85(2):357-368.
22. Appleton B A, Wu P, Maloney J, et al. Structural studies of neuropilin/antibody complexes provide insights into semaphorin and VEGF binding. *EMBO J*. Nov. 28, 2007; 26(23):4902-4912.
23. Vieira J M, Schwarz Q, Ruhrberg C. Role of the neuropilin ligands VEGF164 and SEMA3A in neuronal and vascular patterning in the mouse. *Novartis Found Symp*. 2007; 283:230-235; discussion 235-241.
24. Mima A, Qi W, Hiraoka-Yamomoto J, et al. Retinal not systemic oxidative and inflammatory stress correlated with VEGF expression in rodent models of insulin resistance and diabetes. *Invest Ophthalmol Vis Sci*. Nov. 29, 2012.
25. Chen X L, Nam J O, Jean C, et al. VEGF-induced vascular permeability is mediated by FAK. *Developmental cell*. Jan. 17, 2012; 22(1):146-157.
26. Scheppke L, Aguilar E, Gariano R F, et al. Retinal vascular permeability suppression by topical application of a novel VEGFR2/Src kinase inhibitor in mice and rabbits. *The Journal of clinical investigation*. 2008; 118 (6):2337.
27. Acevedo L M, Barillas S, Weis S M, Göthert J R, Cheresh D A. Semaphorin 3A suppresses VEGF-mediated angiogenesis yet acts as a vascular permeability factor. *Blood*. 2008; 111(5):2674-2680.
28. Eliceiri B P, Paul R, Schwartzberg P L, Hood J D, Leng J, Cheresh D A. Selective requirement for Src kinases during VEGF-induced angiogenesis and vascular permeability. *Molecular cell*. 1999; 4(6):915-924.
29. Hunter T. A tail of two src's: mutatis mutandis. *Cell*. Apr. 10, 1987; 49(1):1-4.
30. Potter M D, Barbero S, Cheresh D A. Tyrosine phosphorylation of V E-cadherin prevents binding of p120-

30. and beta-catenin and maintains the cellular mesenchymal state. *J Biol Chem.* Sep. 9, 2005; 280(36):31906-31912.
31. Calalb M B, Polte T R, Hanks S K. Tyrosine phosphorylation of focal adhesion kinase at sites in the catalytic domain regulates kinase activity: a role for Src family kinases. *Molecular and cellular biology*. February 1995; 15(2):954-963.
32. Schlaepfer D D, Hanks S K, Hunter T, van der Geer P. Integrin-mediated signal transduction linked to Ras pathway by GRB2 binding to focal adhesion kinase. *Nature.* December 22-29, 1994; 372(6508):786-791.
33. Kim J, Oh W J, Gaiano N, Yoshida Y, Gu C. Semaphorin 3E-Plexin-D1 signaling regulates VEGF function in developmental angiogenesis via a feedback mechanism. *Genes Dev.* Jul. 1, 2011; 25(13):1399-1411.
34. Fukushima Y, Okada M, Kataoka H, et al. *Sema*3E-PlexinD1 signaling selectively suppresses disoriented angiogenesis in ischemic retinopathy in mice. *J Clin Invest.* May 2, 2011; 121(5):1974-1985.
35. Sapieha P, Sirinyan M, Hamel D, et al. The succinate receptor GPR91 in neurons has a major role in retinal angiogenesis. *Nature Medicine.* 2008; 14(10):1067-1076.
36. Geretti E, Shimizu A, Klagsbrun M. Neuropilin structure governs VEGF and semaphorin binding and regulates angiogenesis. *Angiogenesis.* 2008; 11(1):31-39.
37. Jones E A, Yuan L, Breant C, Watts R J, Eichmann A. Separating genetic and hemodynamic defects in neuropilin 1 knockout embryos. *Development.* August 2008; 135(14):2479-2488.
38. Kitsukawa T, Shimizu M, Sanbo M, et al. Neuropilin-semaphorin III/D-mediated chemorepulsive signals play a crucial role in peripheral nerve projection in mice. *Neuron.* November 1997; 19(5):995-1005.
39. Kawasaki T, Kitsukawa T, Bekku Y, et al. A requirement for neuropilin-1 in embryonic vessel formation. *Development.* November 1999; 126(21):4895-4902.
40. Dull T, Zufferey R, Kelly M, et al. A third-generation lentivirus vector with a conditional packaging system. *Journal of virology.* November 1998; 72(11):8463-8471.
41. Antipenko A et al. (2003) Structure of the semaphorin-3A receptor binding module. Neuron 39: 589-598.
42. Shirvan A. et al., (2002). Anti-semaphorin 3A Antibodies Rescue Retinal Ganglion Cells from Cell Death following Optic Nerve Axotomy. JBC 277 (51): 49799-49807.

The invention claimed is:

1. A method of preventing or treating macular edema in a subject with non-proliferative retinopathy comprising inhibiting Semaphorin 3A (Sema3A)-mediated ocular vascular hyperpermeability by administering a prophylactically or therapeutically effective amount of at least one Sema3A antagonist selected from the group consisting of:
   i) an anti-Sema3A antibody;
   ii) an anti-Neuropilin-1 (Nrp-1) antibody;
   iii) A Sema3A antisense or shRNA;
   iv) a Nrp-1 antisense or shRNA; and
   v) a soluble Nrp-1 polypeptide or fragment thereof.

2. The method of claim 1, wherein said subject suffers from a) Type II diabetes mellitus (T2DM); b) early stages of diabetes prior to Vascular Endothelial Growth Factor (VEGF), inducement; and/or c) retinal barrier swelling.

3. The method of claim 1, wherein said subject has normal levels of VEGF.

4. The method of claim 1, wherein said subject does not suffer from pericytes loss.

5. The method claim 1, wherein said subject is asymptomatic.

6. The method of claim 1, wherein said a) anti-Nrp-1 antibody or soluble Nrp-1-polypeptide or fragment thereof does not reduce VEGF binding to Nrp-1; b) anti-Nrp-1 antibody binds to the a1a2 domain of Nrp-1; c) Nrp-1 polypeptide fragment consists of the a1a2 domain of Nrp-1; d) anti-Sema3A antibody binds to the Nrp1 binding domain of Sema3A; or e) anti-Sema3A shRNA comprises a sequence as set forth in SEQ ID NO: 3, 4, 5 or 6.

7. The method of claim 1, wherein said Sema3A antagonist specifically targets neurons in the ganglion cell layer (GCL) or inner nuclear layer (INL).

8. The method of claim 6, wherein said Sema3A antagonist specifically targets neurons in the ganglion cell layer (GCL) or inner nuclear layer (INL).

9. The method of claim 1, wherein said Sema3A antagonist is a Sema3A shRNA in a lentiviral vector.

10. The method of claim 1, wherein said Sema3A antagonist is administered intravitreally.

11. The method of claim 1, wherein said Sema3A antagonist is an Nrp-1 polypeptide or fragment thereof and wherein said Nrp-1 polypeptide or fragment thereof is administered intravitreally.

12. The method of claim 1, wherein said Sema3A antagonist is an Nrp-1 polypeptide or fragment thereof and wherein said Nrp-1 polypeptide or fragment thereof is administered intravitreally prior to VEGF-inducement.

13. The method of claim 6, wherein said Sema3A antagonist is an Nrp-1 polypeptide or fragment thereof lacking Nrp-1 domain b1, b2 or b1 and b2 of Npr-1 and wherein said Nrp-1 polypeptide or fragment thereof is administered intravitreally.

* * * * *

SEQUENCE LISTING

<160> NUMBER OF SEQ ID NOS: 15

<210> SEQ ID NO 1
<211> LENGTH: 771
<212> TYPE: PRT
<213> ORGANISM: homosapiens

<400> SEQUENCE: 1

```
Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220
```

-continued

```
Lys Phe Ile Ser Ala His Leu Ile Ser Glu Ser Asp Asn Pro Glu Asp
225                 230                 235                 240

Asp Lys Val Tyr Phe Phe Arg Glu Asn Ala Ile Asp Gly Glu His
            245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
            275                 280                 285

Ala Arg Leu Ile Cys Ser Val Pro Gly Pro Asn Gly Ile Asp Thr His
            290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
                340                 345                 350

Leu Gly Pro Tyr Ala His Arg Asp Gly Pro Asn Tyr Gln Trp Val Pro
            355                 360                 365

Tyr Gln Gly Arg Val Pro Tyr Pro Arg Pro Gly Thr Cys Pro Ser Lys
370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
                420                 425                 430

Gln Ile Val Val Asp Arg Val Asp Ala Glu Asp Gly Gln Tyr Asp Val
            435                 440                 445

Met Phe Ile Gly Thr Asp Val Gly Thr Val Leu Lys Val Val Ser Ile
            450                 455                 460

Pro Lys Glu Thr Trp Tyr Asp Leu Glu Glu Val Leu Leu Glu Glu Met
465                 470                 475                 480

Thr Val Phe Arg Glu Pro Thr Ala Ile Ser Ala Met Glu Leu Ser Thr
                485                 490                 495

Lys Gln Gln Leu Tyr Ile Gly Ser Thr Ala Gly Val Ala Gln Leu
            500                 505                 510

Pro Leu His Arg Cys Asp Ile Tyr Gly Lys Ala Cys Ala Glu Cys Cys
            515                 520                 525

Leu Ala Arg Asp Pro Tyr Cys Ala Trp Asp Gly Ser Ala Cys Ser Arg
            530                 535                 540

Tyr Phe Pro Thr Ala Lys Arg Arg Thr Arg Gln Asp Ile Arg Asn
545                 550                 555                 560

Gly Asp Pro Leu Thr His Cys Ser Asp Leu His His Asp Asn His His
                565                 570                 575

Gly His Ser Pro Glu Glu Arg Ile Ile Tyr Gly Val Glu Asn Ser Ser
            580                 585                 590

Thr Phe Leu Glu Cys Ser Pro Lys Ser Gln Arg Ala Leu Val Tyr Trp
            595                 600                 605

Gln Phe Gln Arg Arg Asn Glu Glu Arg Lys Glu Glu Ile Arg Val Asp
            610                 615                 620

Asp His Ile Ile Arg Thr Asp Gln Gly Leu Leu Leu Arg Ser Leu Gln
625                 630                 635                 640
```

-continued

```
Gln Lys Asp Ser Gly Asn Tyr Leu Cys His Ala Val Glu His Gly Phe
            645                 650                 655

Ile Gln Thr Leu Leu Lys Val Thr Leu Glu Val Ile Asp Thr Glu His
        660                 665                 670

Leu Glu Glu Leu Leu His Lys Asp Asp Gly Asp Gly Ser Lys Thr
        675                 680                 685

Lys Glu Met Ser Asn Ser Met Thr Pro Ser Gln Lys Val Trp Tyr Arg
    690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Arg Gln Arg
                725                 730                 735

Pro Gly His Thr Pro Gly Asn Ser Asn Lys Trp Lys His Leu Gln Glu
            740                 745                 750

Asn Lys Lys Gly Arg Asn Arg Thr His Glu Phe Glu Arg Ala Pro
        755                 760                 765

Arg Ser Val
    770

<210> SEQ ID NO 2
<211> LENGTH: 609
<212> TYPE: PRT
<213> ORGANISM: homosapiens

<400> SEQUENCE: 2

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240
```

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
                340                 345                 350

Tyr Tyr Val Lys Thr Tyr Lys Ile Asp Val Ser Ser Asn Gly Glu Asp
                355                 360                 365

Trp Ile Thr Ile Lys Glu Gly Asn Lys Pro Val Leu Phe Gln Gly Asn
        370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
                420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
    450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Gly Gly Thr Thr Val Leu
            580                 585                 590

Ala Thr Glu Lys Pro Thr Val Ile Asp Ser Thr Ile Gln Ser Gly Ile
                595                 600                 605

Lys

<210> SEQ ID NO 3
<211> LENGTH: 21
<212> TYPE: DNA
<213> ORGANISM: Artificial sequence
<220> FEATURE:
<223> OTHER INFORMATION: Synthetic Construct -continued

```
<400> SEQUENCE: 3
aaatccttga tattaaccag g                                              21

<210> SEQ ID NO 4
<211> LENGTH: 21
<212> TYPE: DNA
<213> ORGANISM: Artificial sequence
<220> FEATURE:
<223> OTHER INFORMATION: Synthetic Construct

<400> SEQUENCE: 4
tttcccgtaa atatcacacc g                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic Construct

<400> SEQUENCE: 5
ttgaaactac tttaagaacg g                                              21

<210> SEQ ID NO 6
<211> LENGTH: 21
<212> TYPE: DNA
<213> ORGANISM: Artificial sequence
<220> FEATURE:
<223> OTHER INFORMATION: Synthetic Construct

<400> SEQUENCE: 6
aaattagcac attctttcag g                                              21

<210> SEQ ID NO 7
<211> LENGTH: 21
<212> TYPE: DNA
<213> ORGANISM: Artificial sequence
<220> FEATURE:
<223> OTHER INFORMATION: Synthetic Construct

<400> SEQUENCE: 7
aaattgccaa tataccaagg c                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic Construct

<400> SEQUENCE: 8
aatgagctgc atgaagtctc g                                              21

<210> SEQ ID NO 9
<211> LENGTH: 21
<212> TYPE: DNA
<213> ORGANISM: Artificial sequence
<220> FEATURE:
<223> OTHER INFORMATION: Synthetic Construct

<400> SEQUENCE: 9
aaattggcac attctttcag g                                              21

<210> SEQ ID NO 10
```

<210> SEQ ID NO 10
<211> LENGTH: 21
<212> TYPE: DNA
<213> ORGANISM: Artificial sequence
<220> FEATURE:
<223> OTHER INFORMATION: Synthetic Construct

<400> SEQUENCE: 10
ttcattagga atacatcctg c    21

<210> SEQ ID NO 11
<211> LENGTH: 21
<212> TYPE: DNA
<213> ORGANISM: Artificial sequence
<220> FEATURE:
<223> OTHER INFORMATION: Synthetic Construct

<400> SEQUENCE: 11
ttatttatag gaaacactgg g    21

<210> SEQ ID NO 12
<211> LENGTH: 923
<212> TYPE: PRT
<213> ORGANISM: human

<400> SEQUENCE: 12

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
```

-continued

```
                260                 265                 270
Phe Lys Cys Met Glu Ala Leu Gly Met Glu Ser Gly Glu Ile His Ser
            275                 280                 285
Asp Gln Ile Thr Ala Ser Ser Gln Tyr Ser Thr Asn Trp Ser Ala Glu
        290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Lys Ile Asp Val Ser Ser Asn Gly Glu Asp
        355                 360                 365
Trp Ile Thr Ile Lys Glu Gly Asn Lys Pro Val Leu Phe Gln Gly Asn
        370                 375                 380
Thr Asn Pro Thr Asp Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
        435                 440                 445
Ser Ser Asn Gln Gly Asp Arg Asn Trp Met Pro Glu Asn Ile Arg Leu
        450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
            500                 505                 510
Arg Lys Phe Lys Ile Gly Tyr Ser Asn Asn Gly Ser Asp Trp Lys Met
        515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
            580                 585                 590
Thr Thr Pro Asn Gly Asn Leu Val Asp Glu Cys Asp Asp Gln Ala
        595                 600                 605
Asn Cys His Ser Gly Thr Gly Asp Asp Phe Gln Leu Thr Gly Gly Thr
        610                 615                 620
Thr Val Leu Ala Thr Glu Lys Pro Thr Val Ile Asp Ser Thr Ile Gln
625                 630                 635                 640
Ser Glu Phe Pro Thr Tyr Gly Phe Asn Cys Glu Phe Gly Trp Gly Ser
                645                 650                 655
His Lys Thr Phe Cys His Trp Glu His Asp Asn His Val Gln Leu Lys
            660                 665                 670
Trp Ser Val Leu Thr Ser Lys Thr Gly Pro Ile Gln Asp His Thr Gly
        675                 680                 685
```

```
Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Gly Asp Lys Asn Ile Ser Arg Lys Pro Gly
        835                 840                 845

Asn Val Leu Lys Thr Leu Asp Pro Ile Leu Ile Thr Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
        915                 920

<210> SEQ ID NO 13
<211> LENGTH: 280
<212> TYPE: PRT
<213> ORGANISM: human

<400> SEQUENCE: 13

Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
```

```
                    130                 135                 140
Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly
        275                 280

<210> SEQ ID NO 14
<211> LENGTH: 923
<212> TYPE: PRT
<213> ORGANISM: mus musculus

<400> SEQUENCE: 14

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
            180                 185                 190

Asp Leu Glu Gln Asp Ser Asn Pro Pro Gly Gly Met Phe Cys Arg Tyr
        195                 200                 205

Asp Arg Leu Glu Ile Trp Asp Gly Phe Pro Glu Val Gly Pro His Ile
    210                 215                 220
```

```
Gly Arg Tyr Cys Gly Gln Lys Thr Pro Gly Arg Ile Arg Ser Ser Ser
225                 230                 235                 240

Gly Val Leu Ser Met Val Phe Tyr Thr Asp Ser Ala Ile Ala Lys Glu
            245                 250                 255

Gly Phe Ser Ala Asn Tyr Ser Val Leu Gln Ser Ser Ile Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Gly Thr Asn Trp Ser Val Glu
        290                 295                 300

Arg Ser Arg Leu Asn Tyr Pro Glu Asn Gly Trp Thr Pro Gly Glu Asp
305                 310                 315                 320

Ser Tyr Lys Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Arg Val Asp Ile Ser Ser Asn Gly Glu Asp
            355                 360                 365

Trp Ile Ser Leu Lys Glu Gly Asn Lys Ala Ile Ile Phe Gln Gly Asn
        370                 375                 380

Thr Asn Pro Thr Asp Val Val Leu Gly Val Phe Ser Lys Pro Leu Ile
385                 390                 395                 400

Thr Arg Phe Val Arg Ile Lys Pro Val Ser Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ala Ser Asn Gln Ala Asp Arg Asn Trp Met Pro Glu Asn Ile Arg Leu
        450                 455                 460

Val Thr Ser Arg Thr Gly Trp Ala Leu Pro Pro Ser Pro His Pro Tyr
465                 470                 475                 480

Thr Asn Glu Trp Leu Gln Val Asp Leu Gly Asp Glu Lys Ile Val Arg
                485                 490                 495

Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Thr
        515                 520                 525

Ile Met Asp Asp Ser Lys Arg Lys Ala Lys Ser Phe Glu Gly Asn Asn
        530                 535                 540

Asn Tyr Asp Thr Pro Glu Leu Arg Thr Phe Ser Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Pro Val Asp Glu Cys Asp Asp Asp Gln Ala
            595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
```

```
                645                 650                 655
His Lys Thr Phe Cys His Trp Glu His Asp Ser His Ala Gln Leu Arg
            660                 665                 670

Trp Ser Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
            690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
                740                 745                 750

Trp Met Val Val Gly His Gln Gly Asp His Trp Lys Glu Gly Arg Val
                755                 760                 765

Leu Leu His Lys Ser Leu Lys Leu Tyr Gln Val Ile Phe Glu Gly Glu
            770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
                835                 840                 845

Asn Val Leu Lys Thr Leu Asp Pro Ile Leu Ile Thr Ile Ile Ala Met
850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Pro Gln Ser Asn Tyr Ser Glu Ala
            915                 920

<210> SEQ ID NO 15
<211> LENGTH: 922
<212> TYPE: PRT
<213> ORGANISM: rattus norvegicus

<400> SEQUENCE: 15

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
                20                  25                  30

Ile Glu Asn Pro Gly Tyr Leu Thr Ser Pro Gly Tyr Pro His Ser Tyr
            35                  40                  45

His Pro Ser Glu Lys Cys Glu Trp Leu Ile Gln Ala Pro Glu Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95
```

-continued

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

Pro Gly Phe Pro Glu Lys Tyr Pro Asn Ser Leu Glu Cys Thr Tyr Ile
                165                 170                 175

Ile Phe Ala Pro Lys Met Ser Glu Ile Ile Leu Glu Phe Glu Ser Phe
                180                 185                 190

Asp Leu Glu Gln Asp Ser Asn Pro Pro Gly Gly Val Phe Cys Arg Tyr
            195                 200                 205

Asp Arg Leu Glu Ile Trp Asp Gly Phe Pro Glu Val Gly Pro His Ile
        210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Ile Ser Glu Asp
                260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Gly Thr Asn Trp Ser Val Glu
        290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Arg Val Asp Ile Ser Ser Asn Gly Glu Asp
        355                 360                 365

Trp Ile Thr Leu Lys Glu Gly Asn Lys Ala Ile Ile Phe Gln Gly Asn
    370                 375                 380

Thr Asn Pro Thr Asp Val Val Phe Gly Val Phe Pro Lys Pro Leu Ile
385                 390                 395                 400

Thr Arg Phe Val Arg Ile Lys Pro Ala Ser Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
        435                 440                 445

Ala Ser Asn Gln Gly Asp Arg Asn Trp Met Pro Glu Asn Ile Arg Leu
    450                 455                 460

Val Thr Ser Arg Thr Gly Trp Ala Leu Pro Pro Ser Pro His Pro Tyr
465                 470                 475                 480

Ile Asn Glu Trp Leu Gln Val Asp Leu Gly Asp Glu Lys Ile Val Arg
                485                 490                 495

Gly Val Ile Ile Gln Gly Gly Lys His Arg Glu Asn Lys Val Phe Met
            500                 505                 510

Arg Lys Phe Lys Ile Ala Tyr Ser Asn Asn Gly Ser Asp Trp Lys Met

```
                515                 520                 525
Ile Met Asp Asp Ser Lys Arg Lys Ala Lys Ser Phe Glu Gly Asn Asn
    530                 535                 540

Asn Tyr Asp Thr Pro Glu Leu Arg Ala Phe Thr Pro Leu Ser Thr Arg
545                 550                 555                 560

Phe Ile Arg Ile Tyr Pro Glu Arg Ala Thr His Ser Gly Leu Gly Leu
                565                 570                 575

Arg Met Glu Leu Leu Gly Cys Glu Val Glu Val Pro Thr Ala Gly Pro
                580                 585                 590

Thr Thr Pro Asn Gly Asn Pro Val Asp Glu Cys Asp Asp Gln Ala
            595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
                660                 665                 670

Trp Arg Val Leu Thr Ser Lys Thr Gly Pro Ile Gln Asp His Thr Gly
            675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu His Tyr Gln Lys Pro Glu Glu Tyr Asp Gln Leu Val
            740                 745                 750

Trp Met Val Val Gly His Gln Gly Asp His Trp Lys Glu Gly Arg Val
            755                 760                 765

Leu Leu His Lys Ser Leu Lys Leu Tyr Gln Val Ile Phe Glu Gly Glu
        770                 775                 780

Ile Gly Lys Gly Asn Leu Gly Gly Ile Ala Val Asp Asp Ile Ser Ile
785                 790                 795                 800

Asn Asn His Ile Pro Gln Glu Asp Cys Ala Lys Pro Thr Asp Leu Asp
            805                 810                 815

Lys Lys Asn Thr Glu Ile Lys Ile Asp Glu Thr Gly Ser Thr Pro Gly
        820                 825                 830

Tyr Glu Glu Gly Lys Gly Asp Lys Asn Ile Ser Arg Lys Pro Gly Asn
            835                 840                 845

Val Leu Lys Thr Leu Asp Pro Ile Leu Ile Thr Ile Ala Met Ser
        850                 855                 860

Ala Leu Gly Val Leu Gly Ala Val Cys Gly Val Val Leu Tyr Cys
865                 870                 875                 880

Ala Cys Trp His Asn Gly Met Ser Glu Arg Asn Leu Ser Ala Leu Glu
                885                 890                 895

Asn Tyr Asn Phe Glu Leu Val Asp Gly Val Lys Leu Lys Asp Lys
                900                 905                 910

Leu Asn Pro Gln Ser Asn Tyr Ser Glu Ala
        915                 920
```